(12) United States Patent
Xu et al.

(10) Patent No.: US 12,318,104 B2
(45) Date of Patent: Jun. 3, 2025

(54) EFFICIENT BACTERIOSTATIC MINIMALLY INVASIVE COLLECTION DEVICES FOR GREAT SAPHENOUS VEIN

(71) Applicant: NANJING DRUM TOWER HOSPITAL, Jiangsu (CN)

(72) Inventors: Can Xu, Nanjing (CN); Dongjin Wang, Nanjing (CN)

(73) Assignee: NANJING DRUM TOWER HOSPITAL, Nanjing (CN)

( * ) Notice: Subject to any disclaimer, the term of this patent is extended or adjusted under 35 U.S.C. 154(b) by 0 days.

(21) Appl. No.: 18/914,008

(22) Filed: Oct. 11, 2024

(65) Prior Publication Data

US 2025/0032145 A1  Jan. 30, 2025

Related U.S. Application Data

(63) Continuation of application No. PCT/CN2023/113339, filed on Aug. 16, 2023.

(30) Foreign Application Priority Data

Sep. 6, 2022 (CN) .......................... 202211081512.6

(51) Int. Cl.
A61B 17/32 (2006.01)
A61B 17/00 (2006.01)
A61B 90/00 (2016.01)

(52) U.S. Cl.
CPC ........ *A61B 17/32* (2013.01); *A61B 17/00234* (2013.01); *A61B 90/08* (2016.02);

(Continued)

(58) Field of Classification Search
CPC ... A61B 17/32; A61B 17/00234; A61B 90/08; A61B 2017/00238; A61B 2017/00398; A61B 2017/00477; A61B 2017/320064
See application file for complete search history.

(56) References Cited

U.S. PATENT DOCUMENTS 6,019,771 A  2/2000  Bennett et al.

FOREIGN PATENT DOCUMENTS

CN  207821880 U  9/2018
CN  212853591 U  4/2021
(Continued)

OTHER PUBLICATIONS

International Search Report in PCT/CN2023/113339 mailed on Dec. 5, 2023, 7 pages.
(Continued)

*Primary Examiner* — Brooke Labranche
(74) *Attorney, Agent, or Firm* — PORUS IP LLC

(57) ABSTRACT

Embodiments of the present disclosure provide an efficient bacteriostatic minimally invasive collection device for great saphenous vein, comprising a grip, a trocar cutting knife, and a protective trocar. The protective trocar is disposed inside the trocar cutting knife, the trocar cutting knife is rotationally connected to the protective trocar; the protective trocar passes through the grip; the grip is provided with a drive mechanism for driving the trocar cutting knife to move relative to the grip; a bacteriostatic cylinder is fixedly mounted at one end of the grip, and the trocar cutting knife passes through the bacteriostatic cylinder; an ultraviolet lamp is fixedly mounted inside the bacteriostatic cylinder, and an end of the bacteriostatic cylinder is provided with a cleaning mechanism for cleaning the trocar cutting knife.

6 Claims, 13 Drawing Sheets

(52) U.S. Cl.
CPC ............... *A61B 2017/00238* (2013.01); *A61B 2017/00398* (2013.01); *A61B 2017/00477* (2013.01); *A61B 2017/320064* (2013.01); *A61B 2217/002* (2013.01)

(56) References Cited

FOREIGN PATENT DOCUMENTS

| | | |
|---|---|---|
| CN | 215231111 U | 12/2021 |
| CN | 215739330 U | 2/2022 |
| CN | 114796813 A | 7/2022 |
| CN | 217090853 U | 8/2022 |
| CN | 115349922 A | 11/2022 |

OTHER PUBLICATIONS

Written Opinion in PCT/CN2023/113339 mailed on Dec. 5, 2023, 8 pages.

EFFICIENT BACTERIOSTATIC MINIMALLY INVASIVE COLLECTION DEVICES FOR GREAT SAPHENOUS VEIN

CROSS REFERENCE TO RELATED APPLICATIONS

This application is a continuation of International Application No. PCT/CN2023/113339, filed on Aug. 16, 2023, which claims the priority of the Chinese application No. 202211081512.6, filed on Sep. 6, 2022, the entire contents of each of which are hereby incorporated by reference.

TECHNICAL FIELD

The present disclosure relates to the technical field of medical devices, and in particular, to an efficient bacteriostatic minimally invasive collection device for great saphenous vein.

BACKGROUND

In bypass surgery, a bridge vessel (target vessel) must be harvested from the patient's body, typically using the saphenous vein or radial artery. In traditional surgery, the skin and muscle tissue are completely dissected to directly visualize and separate the target vessel from the collateral vessels. This procedure usually requires making an incision in the patient's leg or arm equal to the length of the target vessel, typically 20-25 cm. Patients experience significant intraoperative trauma, extended postoperative recovery time, a high risk of infection, intense and prolonged pain, and noticeable scarring after recovery. Current harvesting devices allow doctors to perform minimally invasive surgery on the leg or arm, requiring only one or two small incisions of 1-2 cm in length on the patient's leg or forearm to easily extract the target vessel. This method causes minimal trauma to the patient, reduces the risk of infection and complications, alleviates pain, shortens recovery time, and results in a more aesthetically pleasing outcome.

But usually, when using a collection device to collect blood from a vessel, the trocar cutting knife is directly exposed to the environment. During use, the trocar cutting knife may come into contact with germ-containing objects, leading to poor antimicrobial performance of the knife.

Therefore, there is a need to provide an improved highly efficient bacteriostatic minimally invasive collection device for great saphenous vein to enhance the antimicrobial properties of the trocar cutting knife.

SUMMARY

One or more embodiments of the present disclosure provide an efficient bacteriostatic minimally invasive collection device for great saphenous vein. The device may include a grip, a trocar cutting knife, and a protective trocar; wherein the protective trocar is disposed inside the trocar cutting knife, and the trocar cutting knife is rotationally connected to the protective trocar; the protective trocar passes through the grip; the grip is provided with a drive mechanism for driving the trocar cutting knife to move relative to the grip; a bacteriostatic cylinder is fixedly mounted at one end of the grip, and the trocar cutting knife passes through the bacteriostatic cylinder; an ultraviolet lamp is fixedly mounted inside the bacteriostatic cylinder, and an end of the bacteriostatic cylinder is provided with a cleaning mechanism for cleaning the trocar cutting knife; the cleaning mechanism includes a fixing cap and a cleaning cotton; the fixing cap is threadedly mounted on the end of the bacteriostatic cylinder, the cleaning cotton is disposed in a shape of a ring, the trocar cutting knife passes through the cleaning cotton, and an inner annular wall of the cleaning cotton is in contact with an outer wall of the trocar cutting knife; and a plurality of fixing columns are fixedly mounted on an end wall of the bacteriostatic cylinder, a through-hole is opened in a bottom wall of the fixing cap, a blocking ring is provided in the through-hole, a bottom end of the fixing columns is fixedly connected to the blocking ring, and the trocar cutting knife passes through the blocking ring.

In some embodiments, the drive mechanism includes a threaded pipe and a nut; the threaded pipe is sleeved on the outer wall of the trocar cutting knife and disposed inside the grip; the nut is fixedly mounted inside the grip, the threaded pipe passes through the nut, and the threaded pipe is threadedly connected to the nut; and one end of the threaded pipe away from the nut is sleeved with a first gear, and a drive assembly for driving the first gear to rotate is disposed inside the grip.

In some embodiments, the drive assembly includes a second gear and a motor; the second gear is rotationally mounted inside the grip and meshes with the first gear; and the motor is fixedly mounted in the grip, and an output end of the motor is drivingly connected to the second gear.

In some embodiments, one or more limiting columns are fixedly mounted inside the grip; and at least one of the limiting columns is slidably provided with a slide ring, and the slide ring is fixedly connected to an outer wall of the protective trocar through a connecting bar.

In some embodiments, a fixing mechanism for fixing a guide wire is disposed at a top region of the grip; the fixing mechanism includes a support seat; and the support seat is coaxially disposed with the trocar cutting knife and provided with a groove, the groove is connected to an inner cavity of the grip, two clamping holders are symmetrically disposed in the groove and rotationally connected to the support seat through two connecting columns, the two connecting columns are sleeved with a torsion spring, respectively, and an adjusting plate is fixedly mounted on a side wall of at least one of the two clamping holders.

In some embodiments, each of the two champing holders includes a clamping portion and a rotating portion; the one or more connecting columns are fixedly mounted on the rotating portion, and the clamping portion is disposed in a triangle shape; and the clamping portion is provided with an inclined surface, and the inclined surface is provided with a plurality of fixing projections.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering denotes the same structure, wherein.

DETAILED DESCRIPTION

Figure 1:
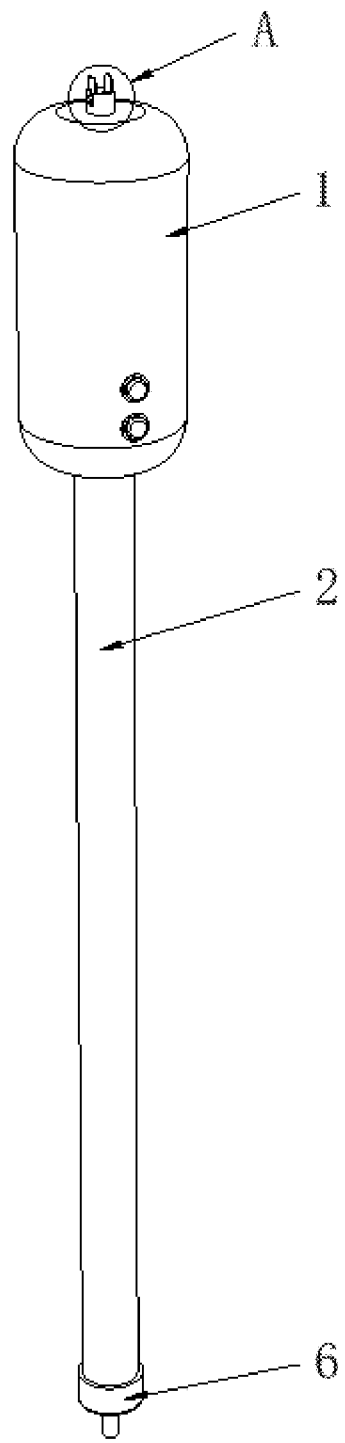
FIG. 1 is a schematic diagram illustrating an efficient bacteriostatic minimally invasive collection device for great saphenous vein according to some embodiments of the present disclosure.

In order to more clearly illustrate the technical solutions of the embodiments of the present disclosure, required the accompanying drawings to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. Unless obviously obtained from the context or the context illustrates otherwise, the same numeral in the drawings refers to the same structure or operation.

It should be understood that as used herein, the terms "system", "device", "unit" and/or "module" are used herein as a way to distinguish between different components, elements, parts, sections, or assemblies at different levels. However, the words may be replaced by other expressions if other words accomplish the same purpose.

As shown in the present disclosure and in the claims, unless the context clearly suggests an exception, the words "a", "an" and/or "the" do not refer specifically to the singular and may include the plural. Generally, the terms "including" and "comprising" suggest only the inclusion of clearly identified steps and elements, and these steps and elements do not constitute an exclusive list, and the method or apparatus may also include other steps or elements.

Figure 2:
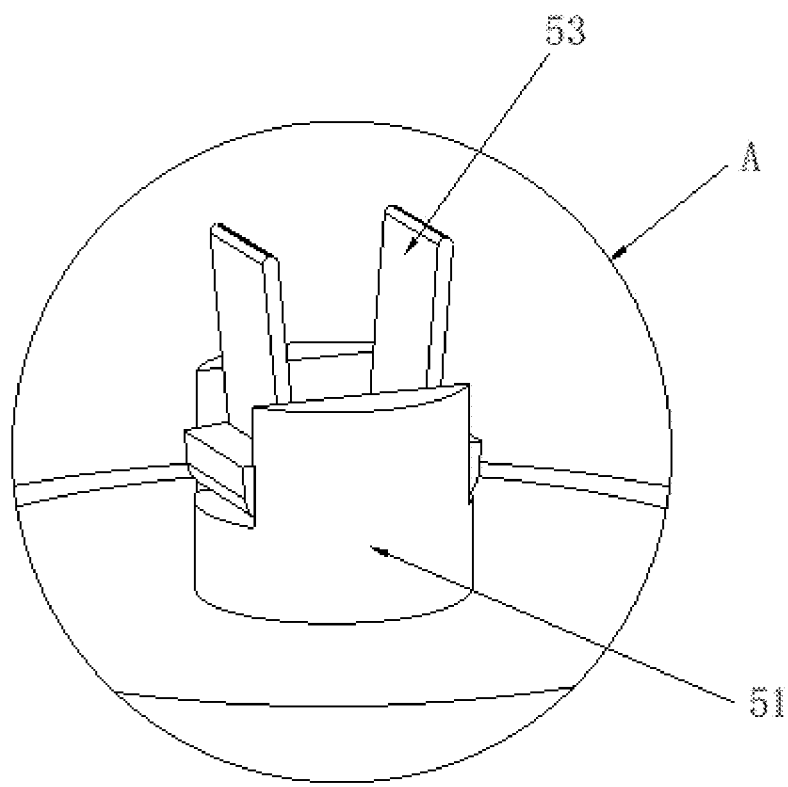
FIG. 2 is an enlarged schematic diagram of a structure at A of FIG. 1.
Figure 3:
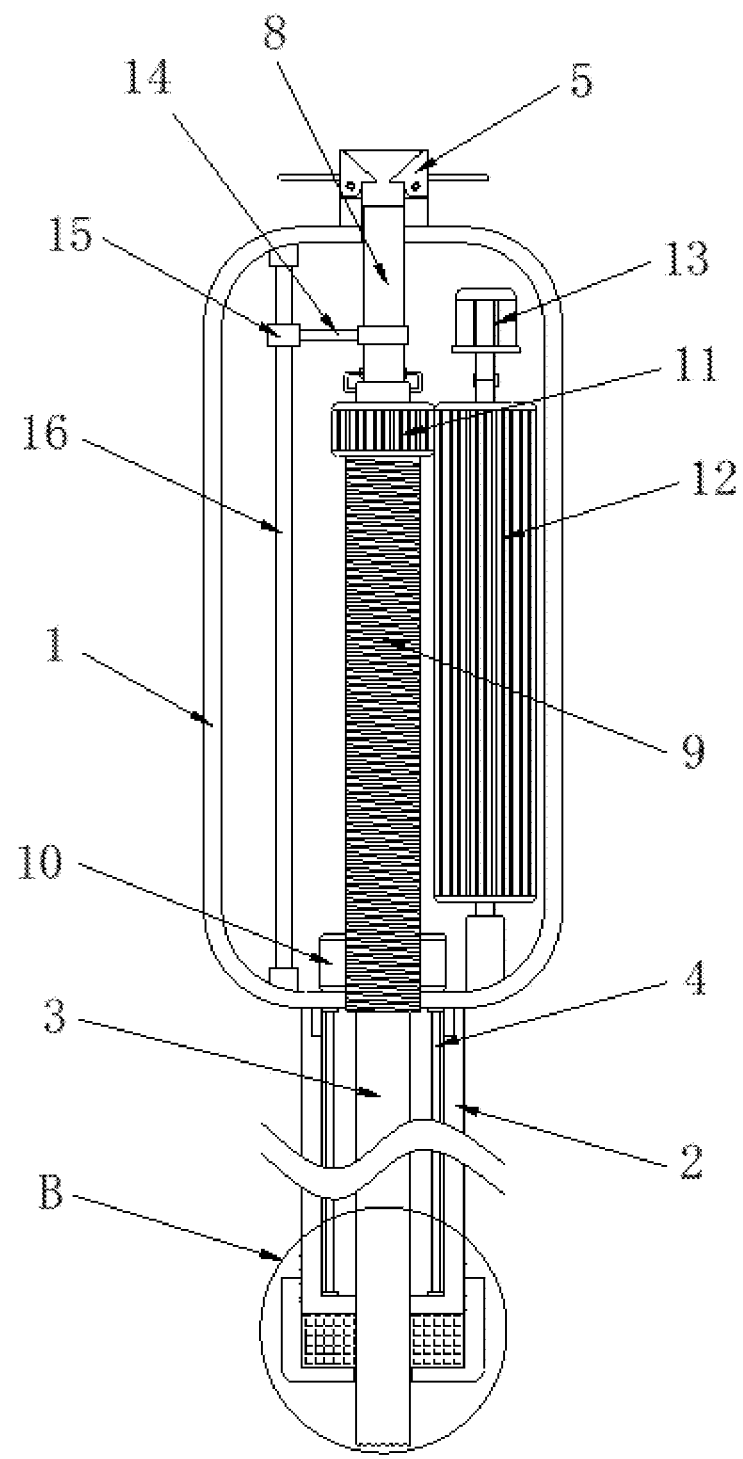
FIG. 3 is a schematic diagram of a cross-sectional structure of an efficient bacteriostatic minimally invasive collection device for great saphenous vein according to some embodiments of the present disclosure.
Figure 4:
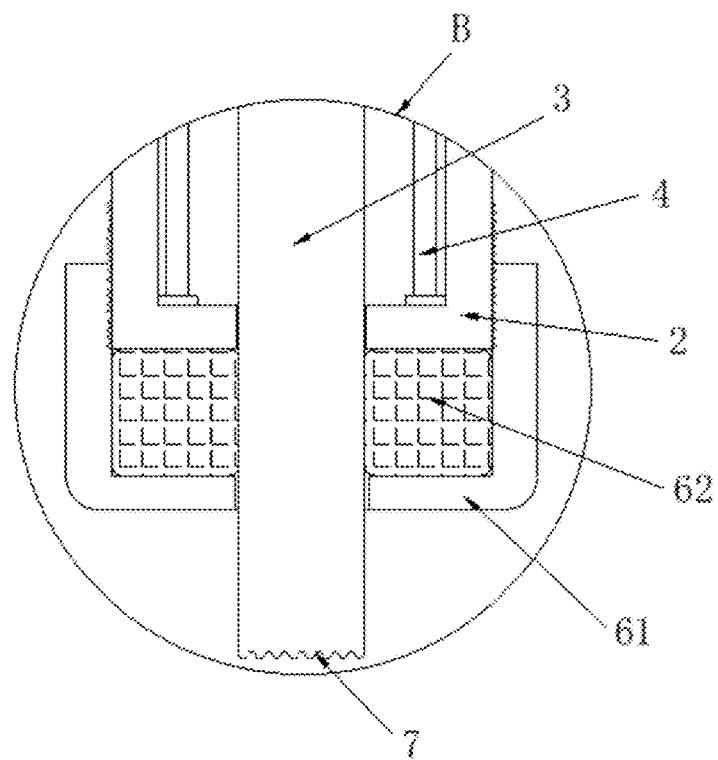
FIG. 4 is an enlarged schematic diagram of a structure at B of FIG. 3.
Figure 5:
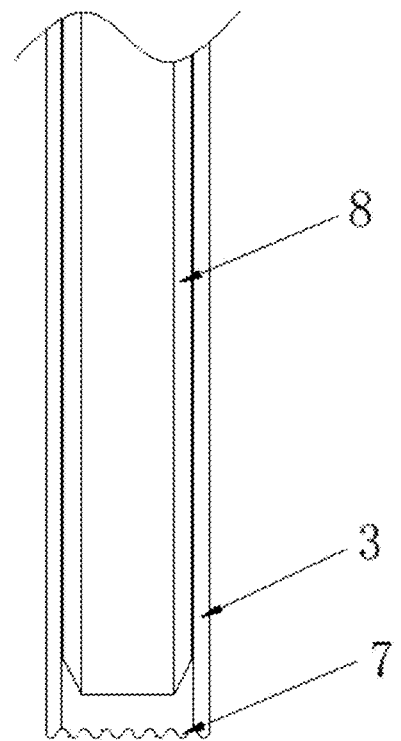
FIG. 5 is a schematic diagram of a cross-sectional structure of trocar cutting knife according to some embodiments of the present disclosure.

FIG. 1 is a schematic diagram illustrating an efficient bacteriostatic minimally invasive collection device for great saphenous vein according to some embodiments of the present disclosure. FIG. 2 is an enlarged schematic diagram of a structure at A of FIG. 1. FIG. 3 is a schematic diagram of a cross-sectional structure of an efficient bacteriostatic minimally invasive collection device for great saphenous vein according to some embodiments of the present disclosure. FIG. 4 is an enlarged schematic diagram of a structure at B of FIG. 3. FIG. 5 is a schematic diagram of a cross-sectional structure of trocar cutting knife according to some embodiments of the present disclosure.

An efficient bacteriostatic minimally invasive collection device for great saphenous vein includes a grip 1, a trocar cutting knife 3, and a protective trocar 8, as illustrated in FIG. 1 and FIG. 3.

The grip 1 refers to a structure that healthcare personnel may hold during surgery. In some embodiments, the grip 1 may include a hollow cylindrical structure.

The protective trocar 8 refers to a tubular structure used to protect a blood vessel. In some embodiments, the protective trocar 8 may move relative to the blood vessel such that the blood vessel may extend inside the protective trocar 8. In some embodiments, the protective trocar 8 is provided inside the trocar cutting knife 3.

In some embodiments, the grip 1 and the protective trocar 8 may be made of a variety of medical materials. For example, the variety of medical materials may include at least one of polyvinyl chloride (PVC), polyethylene (PE), polypropylene (PP), or the like.

The trocar cutting knife 3 refers to a structure that may be used to cut the tissue. For example, the trocar cutting knife 3 may be used to cut the tissue surrounding a blood vessel, separate the blood vessel from the surrounding tissue, or the like. In some embodiments, the trocar cutting knife 3 may be a tubular structure, and the blood vessel may extend into the trocar cutting knife 3.

In some embodiments, the trocar cutting knife 3 may be rotatably connected to the protective trocar 8, i.e., the trocar cutting knife 3 may be rotatable relative to the protective trocar 8. In some embodiments, the protective trocar 8 is not able to slide relative to the trocar cutting knife 3, and the protective trocar 8 and the trocar cutting knife 3 may be move synchronously. For example, the protective trocar 8 may move synchronously along a length direction of the vessel. In the process of moving, the trocar cutting knife 3 may cut the tissue around the blood vessel, and the blood vessel that is separated from the tissue may be extended into the protective trocar 8, avoiding the blood vessel being cut off by being in contact with the trocar cutting knife 3.

In some embodiments, the protective trocar 8 may pass through the grip 1. In some embodiments, the grip 1 is provided with a drive mechanism for driving the trocar cutting knife 3 to move relative to the grip 1.

The drive mechanism may be used to output power to drive the trocar cutting knife 3 and the protective trocar 8 to move synchronously. In some embodiments, the drive mechanism may include different types of structures. For example, the drive mechanism may include at least one of a cylinder, a hydraulic cylinder, a geared drive chain, or the like.

In some embodiments, one end of the grip 1 is fixedly mounted with a bacteriostatic cylinder 2.

The bacteriostatic cylinder 2 refers to a cartridge structure capable of realizing the function of inhibiting bacterial growth. In some embodiments, the trocar cutting knife 3 may pass through the bacteriostatic cylinder 2. The bacteriostatic cylinder 2 may sterilize a portion of the trocar cutting knife 3 that passes through the bacteriostatic cylinder 2. In some embodiments, the bacteriostatic cylinder 2 may be made of a bacteriostatic material. For example, the bacteriostatic material may include at least one of silver, copper, or the like. In some embodiments, the bacteriostatic cylinder 2 may include a bacteriostatic structure. For example, the bacteriostatic structure may include a ultraviolet (UV) lamp or the like.

In some embodiments, at least one ultraviolet (UV) lamp 4 is fixedly mounted inside the bacteriostatic cylinder 2.

The UV lamp 4 may irradiate a UV light onto the trocar cutting knife 3, utilizing the UV light to realize a bacteriostatic effect. In some embodiments, a plurality of UV lamps 4 may be provided and disposed in a ring shape around the circumference of the trocar cutting knife 3. For example, the count of the UV lamps 4 may be two, three, or more.

In some embodiments, the end of the bacteriostatic cylinder 2 is provided with a cleaning mechanism 6 for cleaning the trocar cutting knife 3. In some embodiments, the cleaning mechanism 6 may be used to clean blood from the trocar cutting knife 3. In some embodiments, the cleaning mechanism 6 may include a structure capable of adsorbing blood. For example, the cleaning mechanism 6 may include at least one of a sponge, cotton, gauze, or the like.

In some embodiments, the cleaning mechanism 6 may include a fixing cap 61 and a cleaning cotton 62, as shown in FIG. 4.

The fixing cap 61 may be connected to the bacteriostatic cylinder 2 and serve to fix the cleaning cotton 62. By fixing the cleaning cotton 62, it is possible to prevent the trocar cutting knife 3 from driving the cleaning cotton 62 to move and get inside the tissue as it moves. In some embodiments, the trocar cutting knife 3 may pass through the fixing cap 61 and the cleaning cotton 62. In some embodiments, the fixing cap 61 may be detachably connected to the bacteriostatic cylinder 2 in various ways. For example, the connection between the fixing cap 61 and the bacteriostatic cylinder 2 may include at least one of snap connection, buckle connection, or the like. In some embodiments, the fixing cap 61 may be mounted on the end of the bacteriostatic cylinder 2 via threading, making the fixing cap 61 easy to be installed and replaced.

The cleaning cotton 62 may be used to absorb blood on an outer surface of the trocar cutting knife 3 to prevent blood from remaining on the outer surface of the trocar cutting knife 3. In some embodiments, the cleaning cotton 62 is provided in a ring shape, the trocar cutting knife 3 passes through the cleaning cotton 62, and an inner annular wall of the cleaning cotton 62 is in contact with the outer wall of the trocar cutting knife 3. In some embodiments, the cleaning cotton 62 may be made of a medical sponge.

The collection device may fix the cleaning cotton 62 by the fixing cap 61. When it is necessary to replace the cleaning cotton 62, it is necessary only to unscrew the fixing cap 61, and then take out and replace the cleaning cotton 62. A size of a chamber formed between the fixing cap 61 and the bacteriostatic cylinder 2 may be regulated by rotating the fixing cap 61, thereby adjusting the pressure of the cleaning cotton 62 on the trocar cutting knife 3, and adjusting the cleaning strength.

Figure 6:
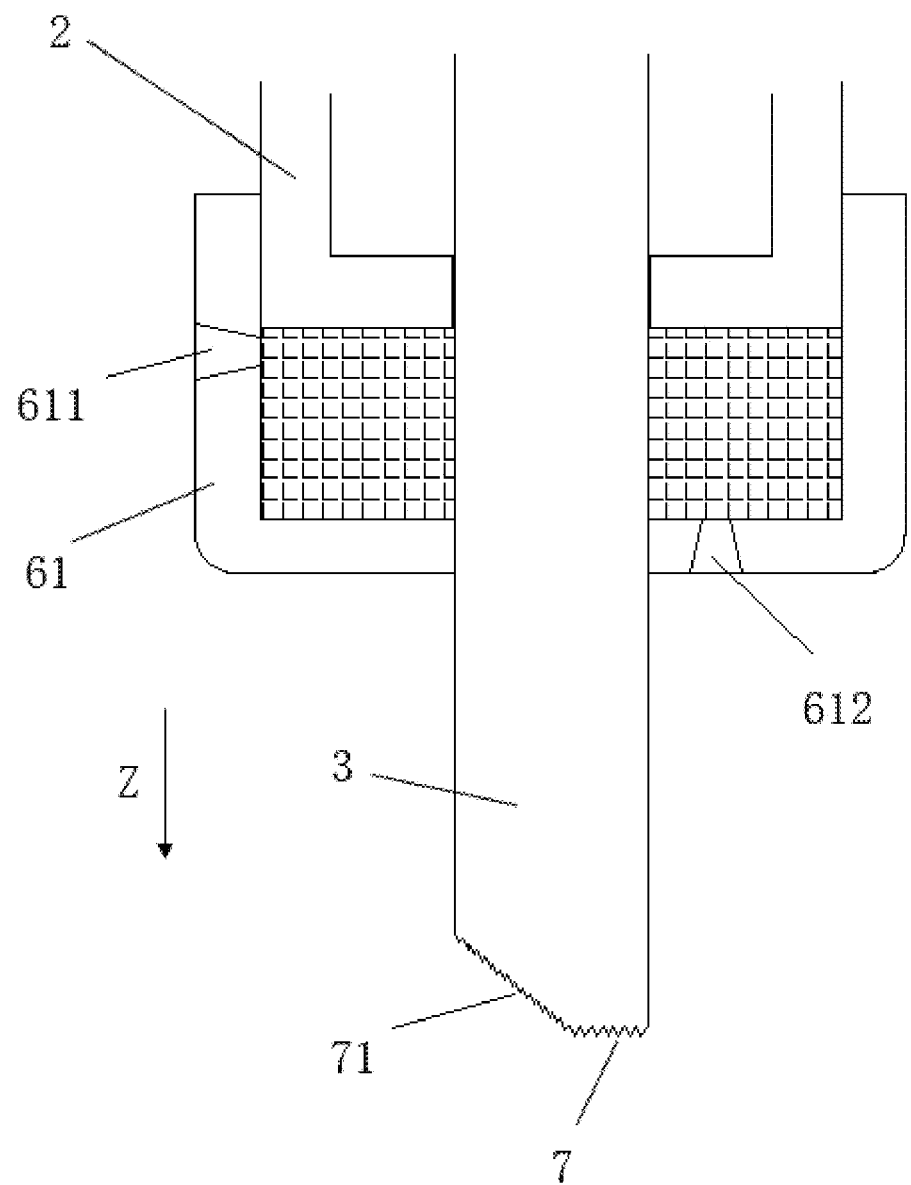
FIG. 6 is a schematic diagram of a structure of a fixing cap according to some embodiments of the present disclosure.

FIG. 6 is a schematic diagram of a structure of a fixing cap according to some embodiments of the present disclosure.

In some embodiments, the fixing cap 61 is provided with an inlet aperture 611 and an outlet aperture 612, as shown in FIG. 6.

The inlet aperture 611 may be used to connect an inlet conduit (not shown in the drawings), and the inlet conduit may be used to deliver a liquid for sterilizing into the fixing cap 61. For example, the inlet conduit may be used to deliver alcohol, disinfectant, or the like.

The outlet aperture 612 may be used to connect an outlet conduit (not shown in the figures), and the outlet conduit may be used to deliver a fluid in the fixing cap 61 outwardly. For example, the outlet conduit may be used to deliver blood, alcohol, or the like, in the fixing cap 61 outwardly.

In some embodiments, the inlet aperture 611 and/or the outlet aperture 612 may utilize a luer fitting.

By providing the inlet aperture 611 to connect the inlet conduit, and the outlet aperture 612 to connect the outlet conduit, it is possible to conveniently deliver alcohol, disinfectant, or the like, from outside to the inside of the fixing cap 61 for disinfecting the cleaning cotton 62, which is not necessary to frequently take out the cleaning cotton 62 in the fixing cap 61.

In some embodiments, the fixing cap 61 may be slidably connected to the bacteriostatic cylinder 2, and a direction in which the fixing cap 61 and the bacteriostatic cylinder 2 may slide relative to each other is parallel to an axial direction of the trocar cutting knife 3 (e.g., the Z-direction of FIG. 6). Through the relative sliding of the fixing cap 61 and the bacteriostatic cylinder 2, it is possible to cause the fixing cap 61 to squeeze the cleaning cotton 62, so that the liquid inside the cleaning cotton 62 may be squeezed out and discharged through the outlet conduit. In addition, the fixing cap 61 may be replaced so that the cleaning cotton 62 resumes its function of absorbing liquid. According to the relative sliding of the fixing cap 61 and the bacteriostatic cylinder 2, there is no need to rotate the fixing cap 61 again, which avoids that the inlet conduit and the outlet conduit are driven to be entangled in the fixing cap 61 when the fixing cap 61 is rotated.

In some embodiments, the inlet aperture 611 and the outlet aperture 612 may be diagonally disposed on the fixing cap 61, such that the inlet aperture 611 and the outlet aperture 612 have the furthest possible distance from each other, which is conducive to sufficiently discharging, during squeezing of the cleaning cotton 62, the cleaning liquid absorbed by the cleaning cotton 62.

In some embodiments, a visual window (not shown in the figures) may be disposed on the fixing cap 61.

The visual window refers to a structure that may be used for viewing from the outside to the inside. For example, the visual window allows for looking from the outside of the fixing cap 61 to the inside of the fixing cap 61. In some embodiments, the visual window may be made of a transparent material. For example, the transparent material may include at least one of transparent plastic, glass, or the like.

By providing a visual window, it is easy for the healthcare personnel to observe the cleaning strength of the cleaning cotton. For example, the size of the chamber formed between the fixing cap 61 and the bacteriostatic cylinder 2 may be viewed through the visual window. It is also possible to view the use of the cleaning cotton 62 so that blood may be squeezed out of the cleaning cotton 62 in a timely manner.

In some embodiments, at least a portion of the visual window may cover the bacteriostatic cylinder 2. That is, the healthcare personnel may view the end of the bacteriostatic cylinder 2 through the visual window, and during a process of squeezing the cleaning cotton 62 by the fixing cap 61, a change in a distance between the fixing cap 61 and the end of the bacteriostatic cylinder 2 may be seen to determine a squeezing degree of the cleaning cotton 62 by the fixing cap 61.

In some embodiments, the fixing cap 61 may be made of a transparent material (e.g., transparent plastic, or the like), and the transparent fixing cap 61 may serve the same purpose as the visual window, thereby enabling direct observation of the inside of the fixing cap 61.

In some embodiments, an input speed of inputting a sterilizing solution through the inlet conduit may be related to a movement direction and a movement speed of the trocar cutting knife 3.

The input speed refers to a flow rate of the disinfectant in the inlet conduit.

The movement direction of the trocar cutting knife 3 and the movement speed of the trocar cutting knife 3 may be obtained from the drive assembly (e.g., the movement direction of the trocar cutting knife 3 may be obtained by reading forward and reverse rotation data of the motor in the drive assembly). In some embodiments, a first input speed of the disinfectant may be positively correlated with the movement speed when the trocar cutting knife 3 is moved along a direction away from the grip 1. For example, the value of the first input speed is larger when the movement speed is faster. When the trocar cutting knife 3 is moved along the direction away from the grip 1, a portion of the trocar cutting knife 3 that contacts the blood is not in contact with the cleaning cotton 62, and the cleaning cotton 62 adsorbs less blood.

In some embodiments, a second input speed of the disinfectant may be positively correlated with the movement speed when the trocar cutting knife 3 is moved along a direction proximate to the grip 1. when the trocar cutting knife 3 is moved along the direction proximate to the grip 1, the portion of the trocar cutting knife 3 that contacts the blood is retracted and in contact with the cleaning cotton 62, and the cleaning cotton 62 adsorbs the blood on the trocar cutting knife 3. When the adsorption is performed and/or after the adsorption is completed, the input speed of the disinfectant may be accelerated, and the disinfectant may be utilized to drain the blood from the cleaning cotton 62 and disinfect the cleaning cotton 62.

In some embodiments, the second input speed may be greater than the first input speed, thereby ensuring cleaning effectiveness.

In some embodiments, the inlet conduit may be connected to a disinfectant storage tank via a control structure, and the control structure may control the rate of disinfectant input. In some embodiments, the control structure may include at least one of a pump, a valve, or the like. In some embodiments, the control structure may be communicatively connected to a remote server. The remote server may collect, analyze, and process the data and generate control instructions to control the control structure to perform a corresponding action or function. For example, the remote server may issue control instructions to the control structure to cause the control structure to perform at least one of the functions of starting up, shutting down, changing the input rate of the disinfectant, or the like. The control structure is utilized to facilitate control of the input speed of the disinfectant, and the control structure may include at least two modes of operation such as automatic control and manual control. When automatic control is used, the healthcare personnel may utilize a remote server to achieve automatic control of the control structure. When manual control is used, the healthcare personnel may manually operate the control structure to achieve manual control. In some embodiments, the control structure may vary the input speed of the disinfectant in a variety of ways. For example, the variety of ways may include at least one of changing the power of the pump, changing a degree of opening of the valve, or the like.

In some embodiments, the remote server may determine the input speed of the disinfectant in a variety of ways. For example, the variety of ways may include querying a preset comparison table. In some embodiments, the preset comparison table may include historical motor rotations and historical movement speeds, and historical input speeds corresponding to the historical motor rotations and the historical movement speeds. In some embodiments, the remote server may construct the preset comparison table based on the historical data. For example, the preset comparison table may be constructed based on the historical motor rotations, the historical movement speeds, and the historical input speeds in the historical data.

The historical motor rotation refers to data related to motor rotation during a historical time period. In some embodiments, the historical motor rotations may include motor forward rotation, reverse rotation, or the like. Further description of the motor may be referenced below.

The historical movement speed refers to a movement speed of the trocar cutting knife 3 when the movement occurs during the historical time period. The historical motor rotation and the historical movement speed may be obtained from the drive assembly.

The historical input speed refers to an input speed of the disinfectant corresponding to the movement of the trocar cutting knife 3 during the historical time period.

In some embodiments, the remote server may query a preset comparison table based on a current motor rotation and a current movement speed to determine a historical motor rotation and a historical movement speed same as the current motor rotation and the current movement speed. The historical input speed corresponding to the historical motor rotation and the historical movement speed may be used as a current input speed.

In some embodiments, the remote server may be set up on a computer in the operating room.

By controlling the input speed of the disinfectant, an amount of the disinfectant input may be reduced to avoid waste or to avoid disinfectant taking up space on the cleaning cotton when the trocar cutting knife is away from the grip. When the trocar cutting knife is close to the grip, the amount of the disinfectant input is increased to improve the efficiency of the disinfectant and ensure that it is in place.

Figure 7:
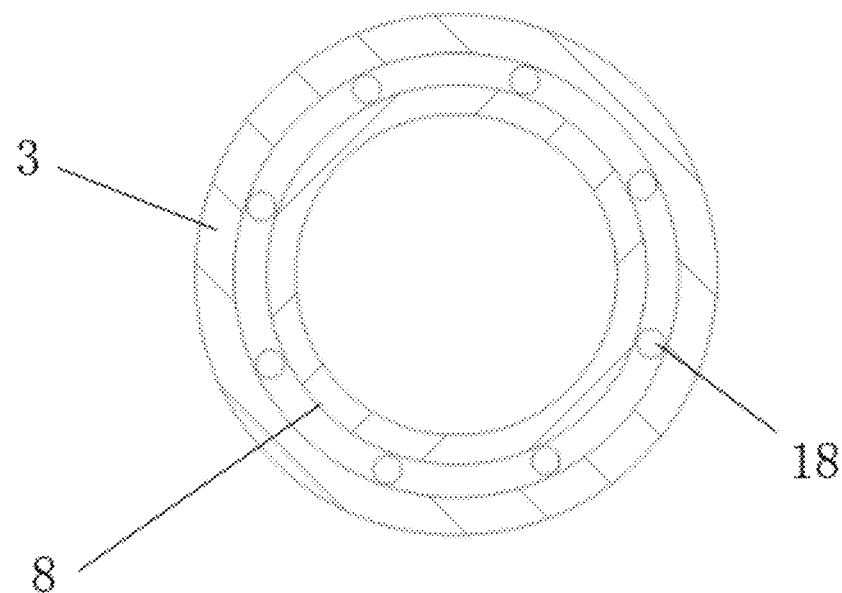
FIG. 7 is a schematic diagram illustrating a structure of a swollen fluid tube according to some embodiments of the present disclosure.
Figure 8:
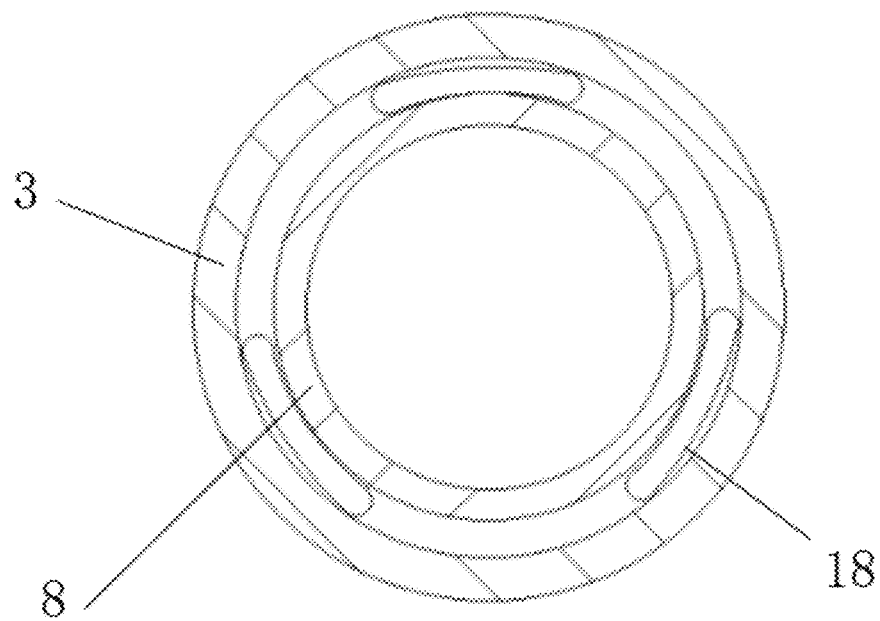
FIG. 8 is a schematic diagram of another structure of a swollen fluid tube according to some embodiments of the present disclosure.

FIG. 7 is a schematic diagram illustrating a structure of a swollen fluid tube according to some embodiments of the present disclosure. FIG. 8 is a schematic diagram of another structure of a swollen fluid tube according to some embodiments of the present disclosure.

In some embodiments, when performing blood vessel harvesting, a swollen fluid may be injected prior to the procedure. By injecting the swollen fluid, a target blood vessel may be swollen and separated from the surrounding tissues for better observation and manipulation of the target blood vessel. After the target vessel is swollen, subsequent operations may be performed.

In some embodiments, the efficient bacteriostatic minimally invasive collection device for great saphenous vein may also include at least one swollen fluid tube 18, as shown in FIG. 7 and FIG. 8.

The swollen fluid tube 18 refers to a tube for delivering the swollen fluid. In some embodiments, the swollen fluid tube 18 may include a variety of structures. For example, the swollen fluid tube 18 may be at least one of a round tube, a flat tube, or the like. In some embodiments, the swollen fluid tube 18 may be made of a variety of materials. For example, the material of the swollen fluid tube 18 may include at least one of PE, PP, PVC, or the like.

In some embodiments, the at least one swollen fluid tube 18 may be fixedly disposed on the outside of the protective trocar 8 and located between the protective trocar 8 and the trocar cutting knife 3. The swollen fluid tube 18 may move synchronously move with the protective trocar 8, avoiding the swollen fluid tube 18 from moving relative to the protective trocar 8 and interfering with the other structures (e.g., a first gear 11, the trocar cutting knife 3, or the like).

In some embodiments, a plurality of swollen fluid tubes 18 may be uniformly distributed along the circumference of the protective trocar 8 so as to avoid collisions and interferences by avoiding structures such as the limiting column 16, the connecting bar 14, or the like.

In some embodiments, one end of the swollen fluid tube 18 may be disposed outside of the fixing mechanism 5. The fixing mechanism 5 may also be used to fix at least a portion of the swollen fluid tube 18. More on the fixing mechanism 5 may be found in the descriptions of FIG. 7-FIG. 11.

In some embodiments, the swollen fluid tube 18 may be connected to an infusion device for inputting the swollen fluid.

The infusion device refers to a device that may be used to deliver a swollen fluid. In some embodiments, the infusion device may include a pump.

In some embodiments, the infusion device may deliver an anesthesia fluid to the swollen fluid tube 18. The swollen fluid tube 18 may deliver the anesthetic fluid into the tissue, thereby anesthetizing the tissue.

The use of the swollen fluid to swell and separate the target blood vessel from the surrounding tissues can improve the efficiency of the trocar cutting knife in cutting the tissues, thereby improving the efficiency of separating the blood vessel. Setting the swollen fluid tube in the protective trocar and the trocar cutting knife allows for the delivery of the swollen fluid using the collection device, and there is no need to remove the swollen fluid tube after the delivery is completed, which can avoid repeated insertion of an external structure into the tissue and reduce the risk of tissue damage and infection. At the same time, additional operating steps may be eliminated, making the procedure more convenient.

In some embodiments, the drive mechanism includes a threaded pipe 9 and a nut 10, as shown in FIG. 3. In some embodiments, the threaded pipe 9 is sleeved around an outer wall of the trocar cutting knife 3.

The threaded pipe 9 refers to a tubular structure having threads. In some embodiments, an outer wall of the threaded pipe 9 has threads. In some embodiments, at least a portion of the threaded pipe 9 is provided inside the grip 1. In some embodiments, the threaded pipe 9 is drivingly connected to the trocar cutting knife 3. For example, when the threaded pipe 9 is rotated and/or moved, the threaded pipe 9 may drive the trocar cutting knife 3 to rotate and/or move synchronously. In some embodiments, the threaded pipe 9 and the trocar cutting knife 3 may be connected in multiple ways. For example, the ways may include at least one of snap connection, bonding, one-piece molding, or the like.

The nut 10 refers to a structure that may be adapted to fit into the threads of the threaded pipe 9.

In some embodiments, the nut 10 may be fixedly mounted inside the grip 1. The threaded pipe 9 may pass through the nut 10, and the threaded pipe 9 is threaded to the nut 10. When the nut 10 moves relative to the threaded pipe 9 rotate, the threaded pipe 9 also moves relative to the nut 10 simultaneously. Because the nut 10 is fixed to the grip 1, the threaded pipe 9 may move along its own axis when the nut 10 rotates relative to the threaded pipe 9.

In some embodiments, the threaded pipe 9 is fitted with the first gear 11 at an end away from the nut 10, and a drive assembly for driving the first gear 11 to rotate is provided within the grip 1. In some embodiments, the threaded pipe 9 and the first gear 11 may be connected in a variety of ways. For example, the ways may include at least one of snap-fitting, bonding, integrally molded, or the like.

In some embodiments, the drive assembly for driving the first gear 11 to rotate is provided within the grip 1.

The drive assembly refers to a structure capable of outputting power. For example, the drive assembly may output a torque to drive the first gear 11 to rotate. In some embodiments, the drive assembly may include a variety of structures. For example, the variety of structures may include at least one of a gear drive chain, a worm gear drive chain, or the like. For more on the drive assembly, see the related description below.

In some embodiments, the drive assembly includes a second gear 12 and a motor 13, the second gear 12 is rotationally mounted inside the grip 1, and the second gear 12 meshes with the first gear 11.

The second gear 12 may be used to drive the first gear 11 to rotate.

In some embodiments, an axial length of the second gear 12 is longer than an axial length of the first gear 11.

When the first gear 11 rotates and drives the threaded pipe 9 to rotate, the threaded pipe 9 may move along an axial direction of the threaded pipe 9, and the first gear 11 may follow the threaded pipe 9 to move synchronously, and in the process of moving the first gear 11, the first gear 11 may always remain engaged with the second gear 12.

The motor 13 may output power. For example, the motor 13 may output a torque to drive the second gear 12 to rotate.

In some embodiments, the motor 13 is fixedly mounted within the grip 1, and an output end of the motor 13 is drivingly connected to the second gear 12.

In some embodiments, a button may be provided on the grip 1, a battery may be provided within the grip 1, and the battery may be electrically connected to the motor 13 via the button. The button may be used to turn on or disconnect the battery from the motor 13, thereby controlling the motor 13 to start up or shut down. In some embodiments, the grip 1 may be provided with two buttons, one of which controls the forward rotation of the output of the motor 13, and the other button controls the reverse rotation of the output of the motor 13. When the motor 13 is turned on, the output end of the motor 13 may drive the second gear 12 to rotate, the second gear 12 may rotate to drive the first gear 11 to rotate, the first gear 11 may rotate to drive the threaded pipe 9 to rotate, and the threaded pipe 9 may be threadedly connected to the nut 10, so that the threaded pipe 9 may move relative to the grip 1 when it rotates, thereby driving the trocar cutting knife 3 to rotate while moving relative to the grip 1, so that the trocar cutting knife 3 may better cut the tissue.

In some embodiments, the end of the trocar cutting knife 3 is provided with a blade 7, as shown in FIG. 5.

The blade 7 refers to a sharp, thin, blade-like structure. By setting the blade 7, the effectiveness of the trocar cutting knife 3 in cutting the tissue may be enhanced. In some embodiments, the blade 7 may be provided at an end of the trocar cutting knife 3 along the circumference of the trocar cutting knife 3. In some embodiments, the blade 7 may be wavy, and the tissue may be cut by the wavy blade 7, which may gradually increase the depth of the blade 7 into the tissue, which is conducive to improving the efficiency of the cutting. In some embodiments, the blade 7 may be connected to the trocar cutting knife 3 in a variety of ways. For example, the ways may include at least one of integrally molded, detachable connection, or the like. For example, the detachable connection may include at least one of snap connection, buckle connection, threaded connection, or the like. In some embodiments, the trocar cutting knife 3 and the blade 7 may be made of a variety of medical materials. For example, the variety of medical materials may include at least one of titanium alloy, stainless steel, or the like.

In some embodiments, at least a portion of the blade 7 may include a beveled blade edge 71.

The beveled blade edge 71 refers to a blade edge that is axially angled with respect to the trocar cutting knife 3. For example, the beveled blade edge 71 may be inclined inwardly from the outer side of the trocar cutting knife 3 along a length direction of the trocar cutting knife 3 (e.g., the Z-direction in FIG. 6). In some embodiments, the beveled blade edge 71 may form a variety of angles with the axis of the trocar cutting knife 3. For example, the angles may include at least one of 30°, 45°, 60°, or the like.

By setting a beveled blade, the area at the end of the trocar cutting knife may be reduced, and when the trocar cutting knife enters the skin incision, the beveled blade may be used to gradually cut through the tissues, which may enhance the cutting effect, and in the process of entering the tissues by the trocar cutting knife, reduce the trauma to the skin incision in a short period of time.

In some embodiments, a limiting column 16 is fixedly mounted within the grip 1, as illustrated in FIG. 3.

The limiting column 16 refers to a structure for restricting the position of the protective trocar 8. In some embodiments, the limiting column 16 may be used to limit the relative rotation of the protective trocar 8 so that the protective trocar 8 may only move and cannot rotate.

In some embodiments, the limiting column 16 may be disposed parallel to the threaded pipe 9. In some embodiments, the limiting column 16 is slidably mounted with a slide ring 15, which is fixedly connected to the outer wall of the protective trocar 8 via a connecting bar 14. By the setting of the limiting column 16 and the slide ring 15, when the threaded pipe 9 is rotated, the threaded pipe 9 transmits the torque to the trocar cutting knife 3, which in turn transmits the torque to the protective trocar 8, and as the protective trocar 8 is fixedly connected to the slide ring 15 by the connecting bar 14, the rotational tendency of the protective trocar 8 to rotate around its own axis is limited, thereby making the protective trocar 8 unable to rotate under the torque of the trocar cutting knife 3; so that the protective trocar 8 may only move relative to the grip 1, and may do not rotate relative to the grip 1, thereby avoiding the trocar cutting knife 3 from driving the protective trocar 8 to rotate when it rotates, and thereby preventing the rotational damage to the blood vessel from the protective trocar 8.

Figure 9:
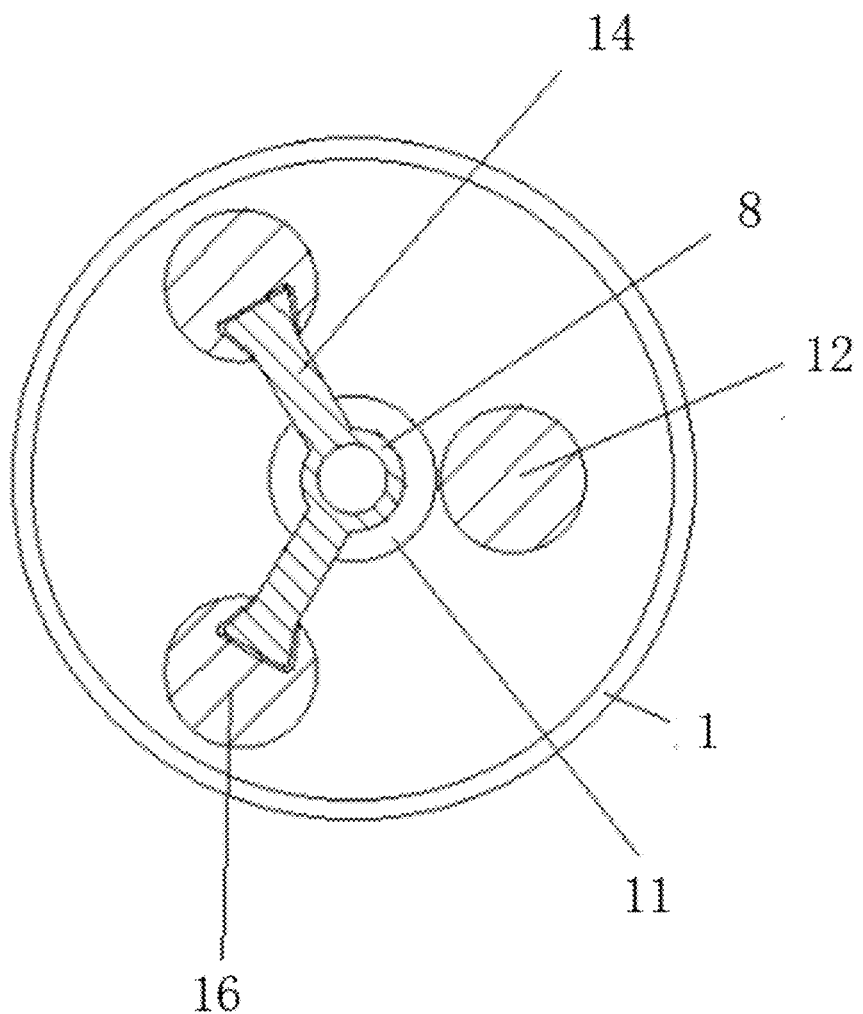
FIG. 9 is a schematic diagram of another structure of a limiting column according to some embodiments of the present disclosure.

FIG. 9 is a schematic diagram of another structure of a limiting column according to some embodiments of the present disclosure.

In some embodiments, as shown in FIG. 9, there are two limiting columns 16, the slide ring 15 is provided on each of the two limiting columns 16, and the protective trocar 8 is connected to the two slide rings 15 by two connecting bars 14. By setting the two limiting columns 16 and the two slide rings 15, it is possible to further enhance the restrictive effect of the slide rings 15 on the protective trocar 8, prevent the protective trocar 8 from rotating, and it is possible to improve the positioning accuracy of the protective trocar 8. The relative position accuracy of the protective trocar 8 and the blood vessel is ensured, and the collision of the protective trocar 8 with the blood vessel during movement is avoided.

In some embodiments, the two limiting columns 16 may be distributed in a circumferential direction of the protective trocar 8. In some embodiments, the two limiting columns 16 and the second gear 12 may be distributed in the circumferential direction of the protective trocar 8. In some embodiments, the two limiting columns 16 and the second gear 12 may be distributed at 120° in the circumferential direction of the protective trocar 8. Utilizing the two limiting columns 16 and the second gear 12 to form a three-directional support for the protective trocar 8, the stability and positional accuracy of the protective trocar 8 may be further improved. The forces exerted by the two limiting columns 16 and the second gear 12 on the protective trocar 8 may also offset each other out, avoiding deformation of the protective trocar 8 by force.

In some embodiments, the connecting bar 14 may be made of an elastic material. For example, the elastic material may include medical rubber, or the like. By adopting an elastic material, the connecting bar 14 is made to have a cushioning and vibration-dampening effect, which may absorb the vibration generated when the second gear 12 is engaged in a transmission with the first gear 11, which is conducive to improving the stability of the protective trocar 8, to prevent the protective trocar 8 from shaking.

Figure 10:
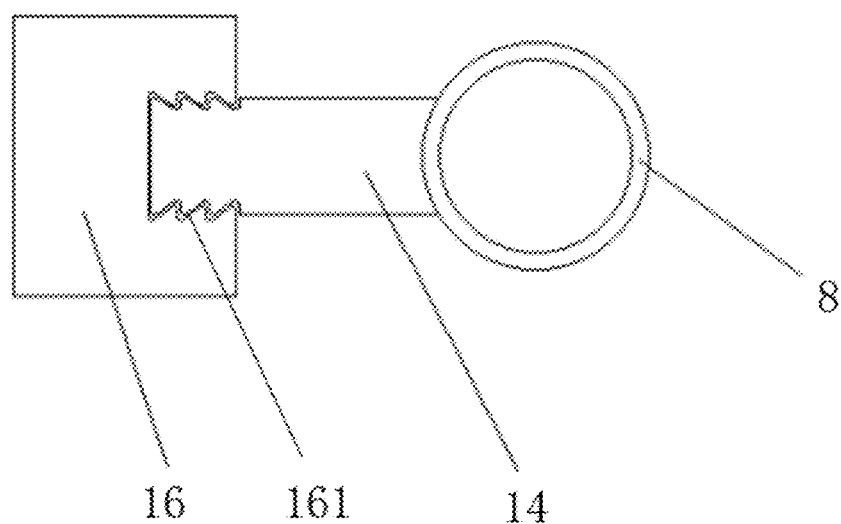
FIG. 10 is a schematic diagram of a connection of a limiting column and a connecting bar according to some embodiments of the present disclosure.

FIG. 10 is a schematic diagram of a connection of a limiting column and a connecting bar according to some embodiments of the present disclosure.

In some embodiments, the limiting column 16 and the connecting bar 14 may be slidably connected, as shown in FIG. 10. In some embodiments, the limiting column 16 is provided with a slide slot 161. In some embodiments, a length direction of the slide slot 161 may be aligned with the axis of the protective trocar 8. In some embodiments, an end of the connecting bar 14 may be slidably connected to the slide slot 161. In this way, the slide ring 15 may be omitted, making the connection structure simpler. At the same time, because the slide ring 15 is in contact with the limiting column 16 in the circumferential direction, there may be the problem that the friction is large, and the slide ring 15 is easily gets stuck on the limiting column 16. According to sliding connection of the limiting column 16 and the connecting bar 14, the friction force is reduced, and it is easier for the limiting column 16 and the connecting bar 14 to slide relative to each other.

In some embodiments, at least one connecting groove may be provided on at least one inner surface of the slide slot 161, and the connecting bar 14 may be provided with a connecting projection that adapts to the at least one connecting groove. Using the fitting of the connecting projections with the connecting grooves, the connecting bar 14 may be prevented from disengaging from the connection with the slide slot 161, and the strength of the connection between the limiting column 16 and the connecting bar 14 may be improved. In some embodiments, a cross-section of the connecting projection may include multiple shapes. For example, the multiple shapes may include at least one of a semicircle, a triangle, a rectangle, or the like.

In some embodiments, toothed grooves are provided on opposing sides of the slide slot 161.

The toothed groove refers to a connecting groove formed by combining a plurality of grooves with a triangular cross-section. The connecting bar 14 is provided with one or more toothed projection adapted to the toothed grooves. By providing the toothed grooves, the area of the inner side of the slide slot 161 may be increased, which correspondingly may increase the contact area of the connecting bar 14 with the slide slot 161, so that when the connecting bar 14 transmits a force to the limiting column 16, the connecting bar 14 may utilize the connection between the connecting bar 14 and the slide slot 161 to disperse the force. By setting the toothed grooves, it is also possible to increase the structural strength of the limiting column 16, enhance the resistance to compression of the limiting column 16, and correspondingly reduce the overall dimension of the limiting column 16, which is conducive to reducing the overall weight of the grip 1.

Figure 11:
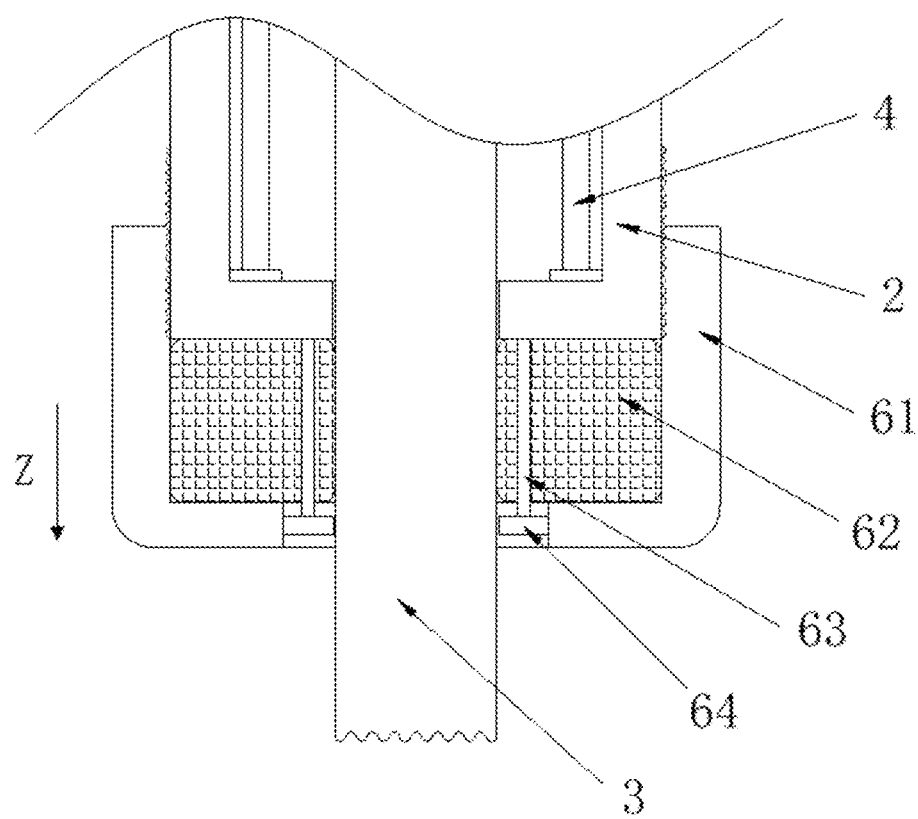
FIG. 11 is a schematic diagram of a sectional structure of a cleaning mechanism according to some embodiments of the present disclosure.

FIG. 11 is a schematic diagram of a sectional structure of a cleaning mechanism according to some embodiments of the present disclosure.

In some embodiments, a plurality of fixing columns 63 are fixedly mounted on the end wall of the bacteriostatic cylinder 2, as shown in FIG. 11. A bottom wall of the fixing cap 61 is open with a through-hole, a blocking ring 64 is provided in the through-hole, and the bottom end of the fixing columns 63 is fixedly connected with the blocking ring 64, and a trocar cutting knife passes through the blocking ring 64.

The end wall of the bacteriostatic cylinder 2 refers to a side wall of the bacteriostatic cylinder 2 away from the grip 1 along an axial direction of the trocar cutting knife 3 (e.g., the Z direction of FIG. 11).

The fixing column 63 may be used to fix the blocking ring 64 so that the blocking ring 64 remains fixed in a relative position to the bacteriostatic cylinder 2. In some embodiments, the plurality of fixing columns 63 may be of the same length so that the blocking ring 64 may be parallel to a end wall of the bacteriostatic cylinder 2. In some embodiments, the plurality of fixing columns 63 may be disposed in a ring around the circumference of the trocar cutting knife 3 to facilitate forming an even support for the blocking ring 64 and improve the stability and positional accuracy of the blocking ring 64.

The blocking ring 64 refers to an annular structure capable of being used to seal a through-hole on the fixing cap 61. In some embodiments, the trocar cutting knife 3 may pass through the blocking ring 64. In some embodiments, the blocking ring 64 may be dynamically scaledly connected to the fixing cap 61 and the trocar cutting knife 3, respectively. The dynamically scaledly connection refers to that the blocking ring 64 and the fixing cap 61, and the blocking ring 64 and the trocar cutting knife 3, may be moved relative to each other and remain scaled during the relative movement. In some embodiments, the blocking ring 64 may be made of an elastic material. For example, the elastic material may include medical rubber, or the like.

When the cleaning cotton 62 absorbs more blood to affect the cleaning effect, a portion of the blood on the cleaning cotton 62 may be squeezed out by tightening the fixing cap 61. When operating, the healthcare personnel may tighten the fixing cap 61, so that the fixing cap 61 squeezes the cleaning cotton 62, and at the same time, when the fixing cap 61 is moved, the blocking ring 64 is moved out of the through-hole, so that the blood squeezed from the cleaning cotton 62 may flow out through the through-hole, which is more convenient to squeeze out the blood for cleaning. Meanwhile, by setting the blocking ring 64, it is difficult for the blood on the cleaning cotton 62 to overflow through the through-hole during the surgical process.

Figure 12:
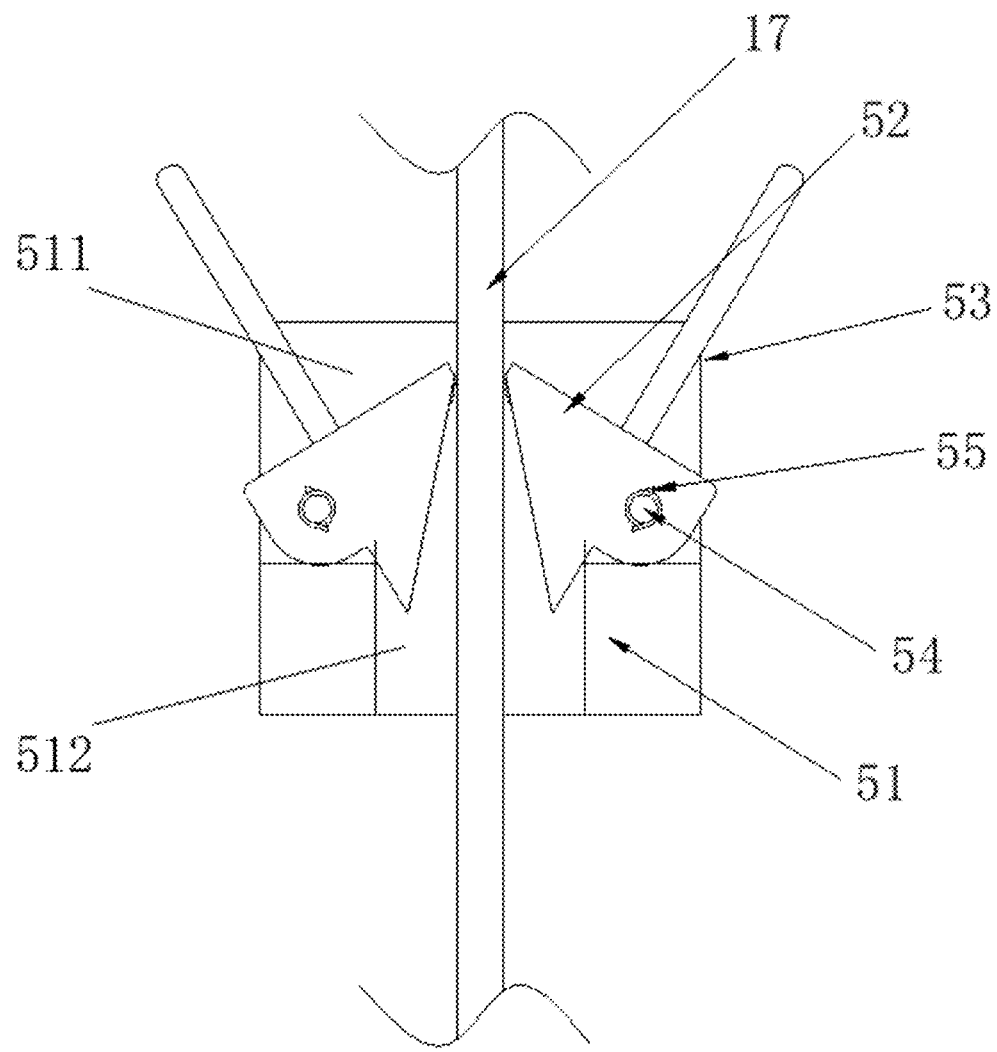
FIG. 12 is a schematic diagram of a cross-sectional structure of a fixing mechanism according to some embodiments of the present disclosure when a guide wire is fixed.
Figure 13:
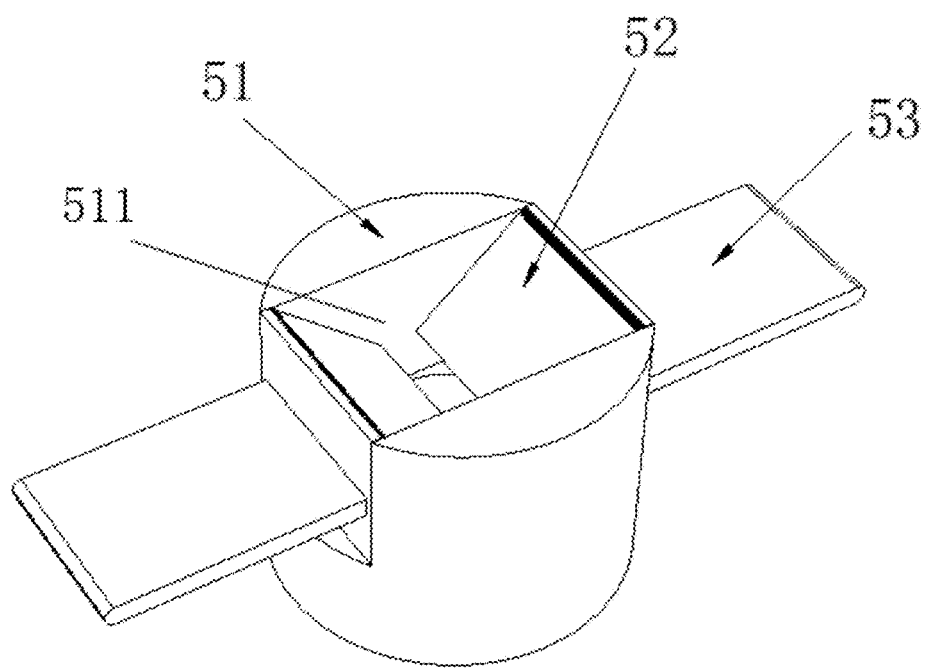
FIG. 13 is a schematic diagram of a three-dimensional structure of a fixing mechanism according to some embodiments of the present disclosure when a guide wire is fixed.
Figure 14:
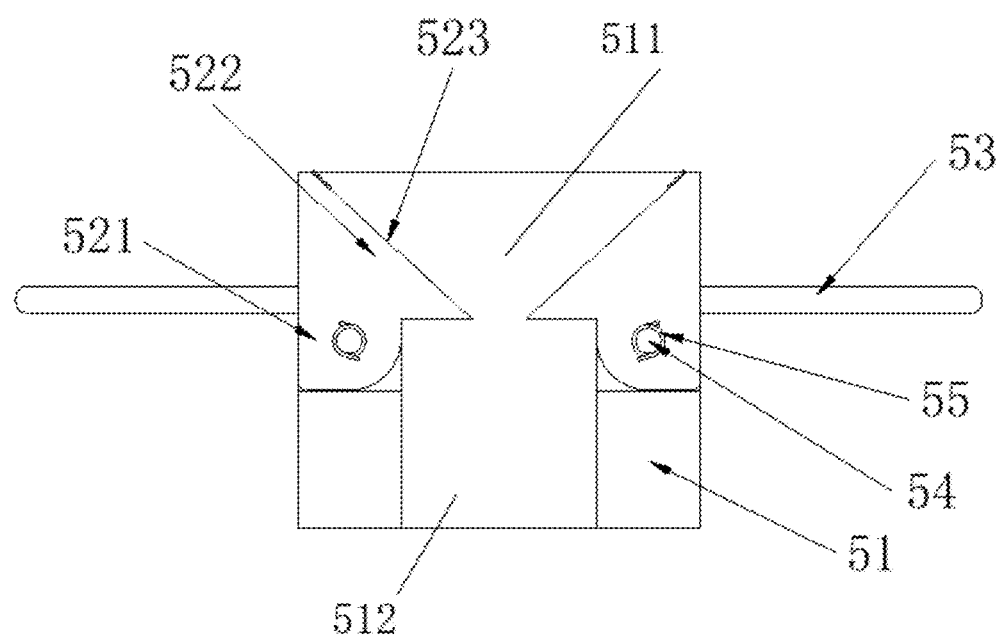
FIG. 14 is a schematic diagram of a sectional structure of a fixing mechanism during threading of a guide wire according to some embodiments of the present disclosure.
Figure 15:
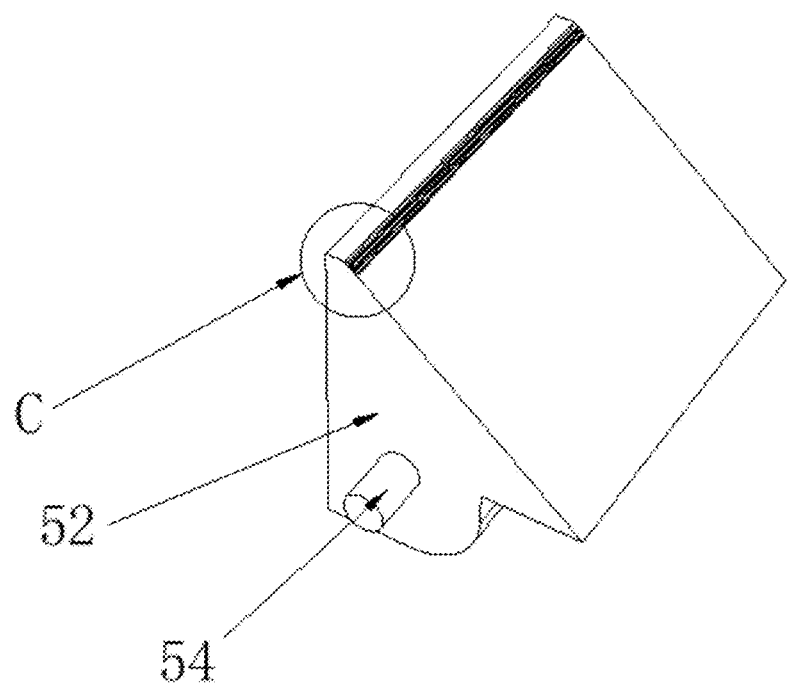
FIG. 15 is a schematic diagram of a three-dimensional structure of a clamping holder according to some embodiments of the present disclosure.
Figure 16:
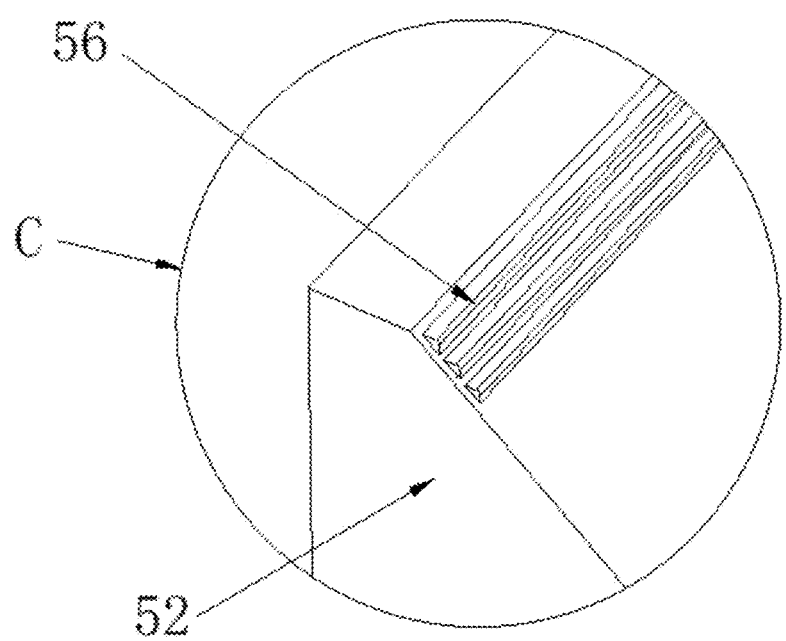
FIG. 16 is an enlarged schematic of a structure at C of FIG. 15.

FIG. 12 is a schematic diagram of a cross-sectional structure of a fixing mechanism according to some embodiments of the present disclosure when a guide wire is fixed. FIG. 13 is a schematic diagram of a three-dimensional structure of a fixing mechanism according to some embodiments of the present disclosure when a guide wire is fixed. FIG. 14 is a schematic diagram of a sectional structure of a fixing mechanism during threading of a guide wire according to some embodiments of the present disclosure. FIG. 15 is a schematic diagram of a three-dimensional structure of a clamping holder according to some embodiments of the present disclosure. FIG. 16 is an enlarged schematic of a structure at C of FIG. 15.

In some embodiments, as shown in FIG. 2, FIG. 11-FIG. 16, the fixing mechanism 5 for fixing the guide wire 17 is provided at the top of the grip 1. By adopting the fixing mechanism for fixing the guide wire 17, the stability of the guide wire 17 as well as the positional accuracy may be improved, so as to ensure the guide effect of the guide wire 17 on the trocar cutting knife 3 and ensure the quality of the surgery. In some embodiments, the fixing mechanism 5 may fix the guide wire 17 in a plurality of ways. For example, the ways may include at least one of snap connection, buckle connection, or the like.

In some embodiments, the fixing mechanism 5 may include a support seat 51, the support seat 51 may be coaxially disposed with the trocar cutting knife 3, the support seat 51 is provided with a groove 511, the groove 511 is connected to an inner cavity of the grip 1 by a through-hole 512, and the guide wire 17 may pass through the groove 511 to enter the inner cavity of the grip 1. In some embodiments, the groove 511 may include two opposing inner sides and a bottom surface, and the through-hole 512 in the support seat 51 is provided on the bottom surface of the groove 511. In some embodiments, the two opposing inner sides may be parallel to each other. In some embodiments, the inner sides may be perpendicular to the bottom surface.

In some embodiments, two clamping holders 52 are symmetrically disposed within the groove 511, and the two clamping holders 52 may be rotationally connected to the support seat 51 via the connecting column 54. In some embodiments, two ends of the connecting columns 54 are connected to two inner sides. In some embodiments, the clamping holders 52 may rotate with the axis of the connecting column 54 as the center of rotation. In some embodiments, the two connecting columns 54 corresponding to the two clamping holders 52 may be located on two sides of the through-hole 512 in the support seat 51. In some embodiments, the two connecting columns 54 corresponding to the two clamping holders 52 may be parallel to each other. In some embodiments, the two clamping holders 52 may rotate in reverse, e.g., rotating both inwardly or both outwardly. When simultaneously rotated inwardly, the two clamping holders 52 may become closed to clamp the guide wire 17.

When simultaneously rotated outwardly, the two clamping holders 52 may change to an open state to loosen the guide wire 17.

In some embodiments, torsion springs 55 are packaged on both connecting columns 54. The torsion springs 55 is a flexible structure. In some embodiments, the torsion springs 55 may be connected between the connecting columns 54 and the support seat 51. The torsion springs 55 may apply a spring force to the connecting columns 54 that causes the connecting columns 54 to rotate inwardly or outwardly.

In some embodiments, one end of the torsion springs 55 is fixedly connected to the connecting columns 54, and the other end of the torsion springs 55 is fixedly connected to the support seat 51. In some embodiments, by providing the torsion springs 55, when the torsion springs 55 are in a natural state, the two clamping holders 52 may be made to fit and squeeze together to form a closed state.

In some embodiments, an adjusting plate 53 is fixedly mounted to a side wall of the clamping holder 52. At least a portion of the adjusting plate 53 may extend out of the groove 511 of the support seat 51. By pressing down on the adjusting plate 53, the spring force of the torsion springs 55 may be counteracted to cause the two clamping holders 52 to separate from each other.

In some embodiments, the clamping holder 52 includes a clamping portion 522 and a rotating portion 521, as shown in FIG. 14.

The clamping portion 522 refers to a portion of the clamping holder 52 that may be used to clamp the guide wire. In some embodiments, the connecting columns 54 are fixedly mounted to the rotating portion 521. In some embodiments, the clamping portion 522 is provided in a triangular shape. For example, the clamping portion 522 may be set in a triangular shape. The edges of the clamping portion 522 may be parallel to the connecting columns 54. In some embodiments, the clamping portion 522 may be provided in the shape of a right-angled trigonal prism. In some embodiments, the surfaces corresponding to the beveled edges of the two clamping portions 522 may be provided facing inwardly. The side corresponding to one of the right-angled edges of the clamping portion 522 is connected to the rotating portion 521.

At least a portion of the sides of the rotating portion 521 may include a cylindrical surface. In some embodiments, an axis of the cylindrical surface may coincide with an axis of the connecting column 54. In some embodiments, the cylindrical surface may include a quarter-cylindrical surface. In some embodiments, a distance between the axis of the connecting column 54 and the bottom surface of the groove 511 may be greater than or equal to a radius of the cylindrical surface. By providing the cylindrical surface, it is possible to avoid the outer surface of the rotating portion 521 from interfering with the bottom surface of the groove 511, which may result in the rotating portion 521 being unable to rotate. The use of a quarter cylindrical surface may limit the rotation angle of the rotating portion 521 and avoid unnecessary rotation of the rotating portion 521.

In some embodiments, at least a portion of the side of the rotating portion 521 may be tangent to a cylindrical surface. In some embodiments, at least a portion of the sides of the clamping portion 522 may extend beyond the cylindrical surface. In some embodiments, the portion of the side tangent to the cylindrical surface, and the portion of the side that extends beyond the cylindrical surface are located on two sides of the cylindrical surface along the circumference, respectively. In this way, the angle of rotation of the rotating portion 521 may be further limited, and the control accuracy of the rotation of the rotating portion 521 may be improved.

In some embodiments, an inclined surface 523 may be provided on the clamping portion 522. For example, when the clamping portion 522 is provided in the shape of a right-angled triangular prism, the side corresponding to the sloping edge is the inclined surface 523.

In some embodiments, as shown in FIG. 13 and FIG. 14, a plurality of fixing projections 56 may be provided on the inclined surface 523, and when fixing the guide wire 17, the fixing projections 56 are pressed against the guide wire 17 so as to fix it. The fixing projections 56 may be used to increase the friction between the inclined surface 523 and the guide wire 17, so as to enhance the fixing effect of the clamping portion 522 on the guide wire 17, which is conducive to preventing the guide wire 17 from loosening and affecting the quality of the surgery.

In some embodiments, the fixing projections 56 may be made of a non-slip and flexible rubber material.

Figure 17:
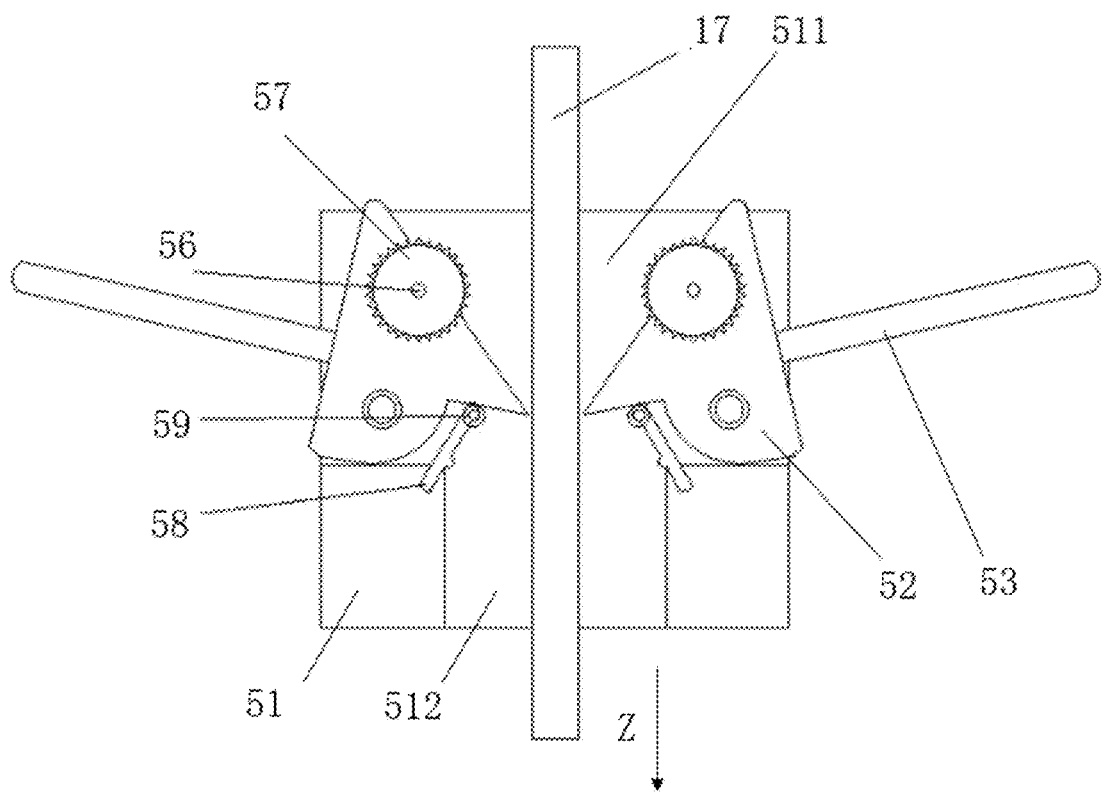
FIG. 17 is a schematic diagram of a structure of a guide wire delivery device according to some embodiments of the present disclosure.
Figure 18:
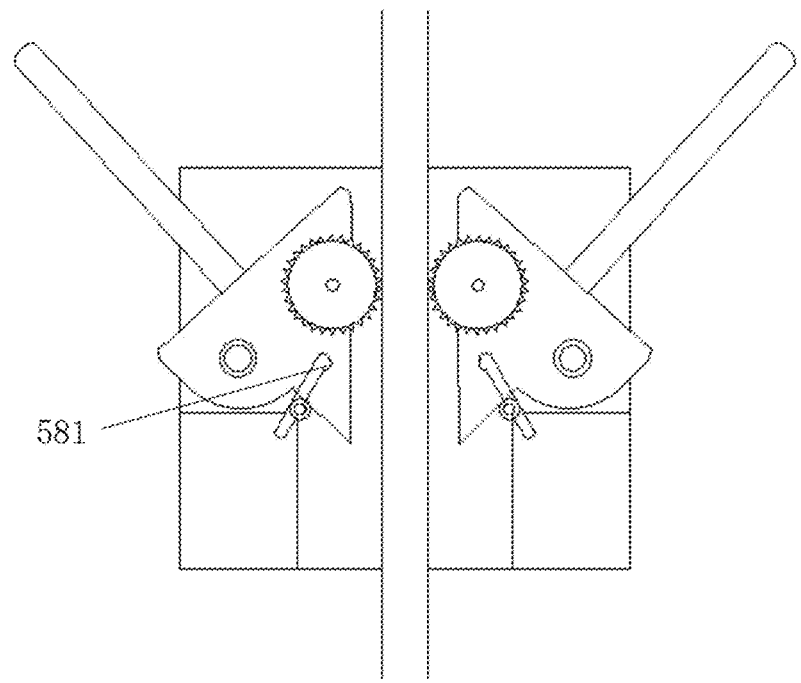
FIG. 18 is a schematic diagram of a structure of a guide wire delivery device in a conveying state according to some embodiments of the present disclosure.
Figure 19:
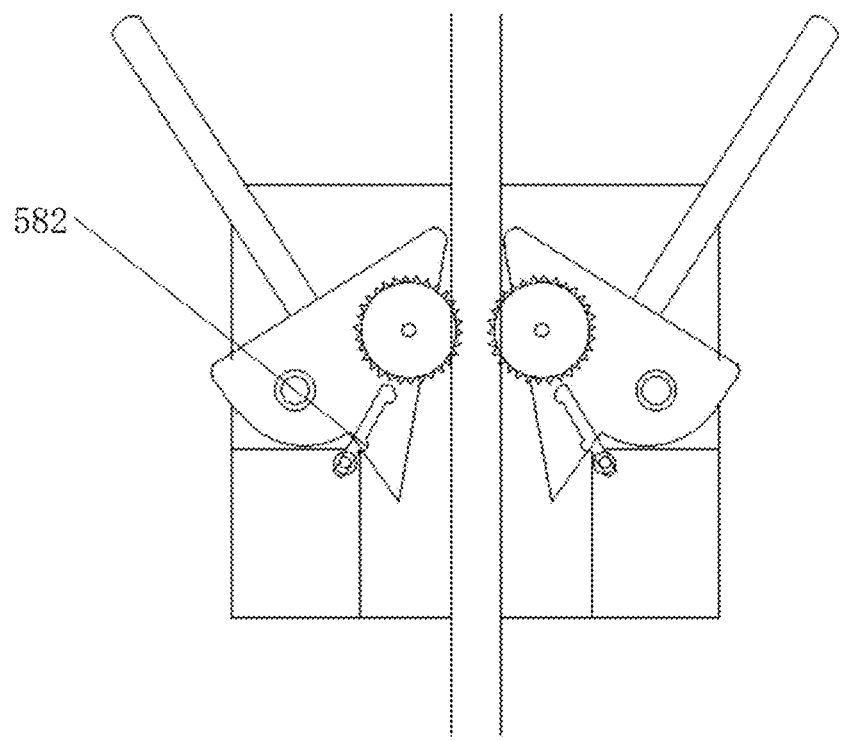
FIG. 19 is a schematic diagram of a structure of a guide wire delivery device in a locked state according to some embodiments of the present disclosure.
Figure 20:
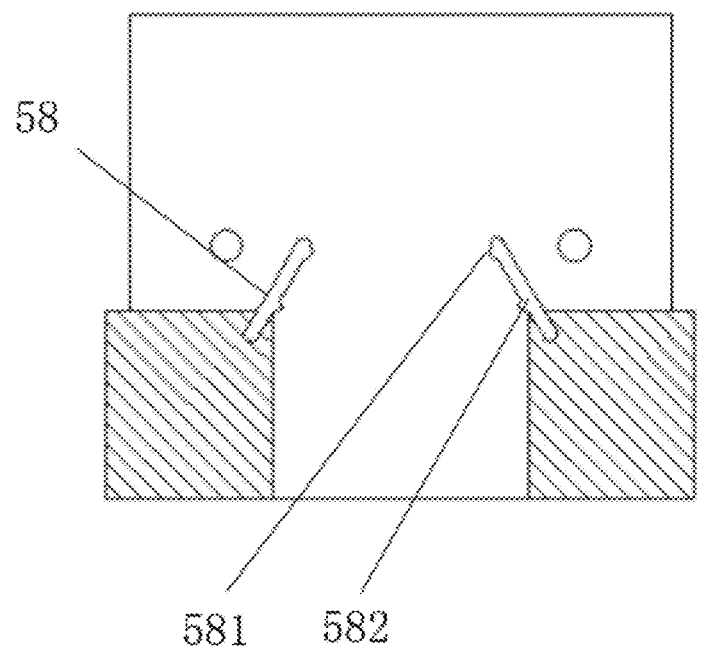
FIG. 20 is a schematic diagram of a structure of a limit slot according to some embodiments of the present disclosure.

FIG. 17 is a schematic diagram of a structure of a guide wire delivery device according to some embodiments of the present disclosure. FIG. 18 is a schematic diagram of a structure of a guide wire delivery device in a conveying state according to some embodiments of the present disclosure. FIG. 19 is a schematic diagram of a structure of a guide wire delivery device in a locked state according to some embodiments of the present disclosure. FIG. 20 is a schematic diagram of a structure of a limit slot according to some embodiments of the present disclosure.

In some embodiments, the fixing mechanism 5 may further include a guide wire delivery device.

The guide wire delivery device may be used to apply a force to the guide wire 17 to move the guide wire 17. In some embodiments, a direction of the force applied by the guide wire delivery device on the guide wire 17 is parallel to a length direction of the guide wire 17 (e.g., the Z direction in FIG. 17).

In some embodiments, as shown in FIGS. 17-20, the guide wire delivery device may include two guide wire delivery gears 57, with each of the two guide wire delivery gears 57 being rotatably connected to the clamping holder 52 via a gear shaft 56.

The guide wire delivery gear 57 refers to a wheel-like structure with at least one tooth provided on a circumferential surface. In some embodiments, the guide wire delivery gear 57 may be in rolling contact with the guide wire 17. When the guide wire delivery gear 57 is in rolling contact with the guide wire 17, the guide wire 17 may move based on the rotation of the guide wire delivery gear 57. The teeth on the guide wire delivery gear 57 may increase the friction between the guide wire delivery gear 57 and the guide wire 17, preventing the guide wire delivery gear 57 from slipping with the guide wire 17.

The gear shaft 56 serves as a mounting base that may be used to mount the guide wire delivery gear 57.

In some embodiments, the two guide wire delivery gears 57 may be symmetrically disposed on two sides of the guide wire 17, and the two guide wire delivery gears 57 may be rotatably connected to the two clamping holders 52. When the two clamping holders 52 rotate, a relative distance between the two guide wire delivery gears 57 may be varied so that the guide wire delivery gears 57 are in contact or out of contact with the guide wire 17. In some embodiments, the guide wire delivery gears 57 may be made of an elastic material. For example, the elastic material may include medical rubber, or the like. The guide wire delivery gear 57 is made of an elastic material, which may form an elastic contact with the guide wire 17, thereby increasing the friction between the guide wire delivery gear 57 and the guide wire 17, which can further prevent the guide wire delivery gear 57 and the guide wire 17 from slipping.

In some embodiments, as shown in FIG. 17 and FIG. 20, the guide wire delivery device may further include a limit slot 58 and a limit block 59. The limit block 59 is slidably connected to the limit slot 58. The limit block 59 is provided on the clamping holder 52, and the limit slot 58 is provided on at least one side of the groove 511. In some embodiments, there may be two limit slots 58 and two limit blocks 59, respectively, and the two limit slots 58 may be symmetrically disposed on both sides of the guide wire 17, and the two limit blocks 59 may be are correspondingly connected to the two limit slots 58.

The limit slot 58 may be used to act as a restriction on the limit block 59, for example, restricting at least one position of the limit block 59, restricting a movement route of the limit block 59, or the like. In some embodiments, the limit slot 58 is provided with a first groove feature 581 and a second groove feature 582, as shown in FIG. 18.

The first groove feature 581 and the second groove feature 582 refer to grooves that project outwardly with respect to the limit slot 58. In some embodiments, the first groove feature 581 may be provided at an end of the limit slot 58 away from the grip 1. In some embodiments, the second groove feature 582 may be provided at a middle position of the limit slot 58.

In some embodiments, as shown in FIG. 17, the limit block 59 may snap to the first groove feature 581 to form the guide wire delivery device in a mounted state. When the guide wire delivery device is in the mounted state, the minimum distance between the two guide wire delivery gears 57 is greater than the diameter of the guide wire 17, and the guide wire 17 may pass through the gap between the two guide wire delivery gears 57 and enter the protective trocar 8. The guide wire delivery gears 57 may play a guiding role in the movement of the guide wire 17, facilitating the quick installation of the guide wire 17.

In some embodiments, as shown in FIG. 18, the limit block 59 may snap to the second groove feature 582 such that the guide wire delivery device is in a conveying state. When the guide wire delivery device is in the conveying state, the minimum distance between the two guide wire delivery gears 57 may be equal to the diameter of the guide wire 17, the guide wire delivery gears 57 may abut against the guide wire 17, and by rotating the guide wire delivery gears 57, the guide wire delivery gears 57 may form a rolling connection with the guide wire 17, thereby driving the guide wire 17 to move.

In some embodiments, as shown in FIG. 19, the limit block 59 may snap to the end of the limit slot 58 proximate to the grip 1 to form a locked state of the guide wire delivery device. When the guide wire delivery device is in the locked state, the two guide wire delivery gears 57 may clamp the guide wire 17, so that the end of the guide wire 17 that is located within the fixing mechanism 5 remains fixed. In some embodiments, the guide wire delivery gears 57 may be made of a resilient material, and when the guide wire delivery device is in the locked state, the guide wire delivery gears 57 may be adaptively and resiliently deformed to avoid the guide wire delivery gears 57 from damaging the guide wire 17.

In some embodiments, the limit block 59 may be made of an elastic material. For example, the elastic material may include medical rubber or the like. In some embodiments, the limit block 59 is in a first pressurized state and adaptively elastically deforms when the limit block 59 is disposed within the limit slot 58. When the limit block 59 is snapped to the first groove feature 581 or snapped to the second groove feature 582, the limit block 59 may be in a natural state or a second pressurized state. But a degree of elastic deformation of the second pressurized state is less than a degree of elastic deformation of the first pressurized state.

In some embodiments, the limit slot 58 may be a linear groove. The use of a linear groove has the advantage of being easy to machine. The amount of elastic deformation of the limit block 59 gradually changes during relative movement of the limit block 59 and the limit slot 58.

In some embodiments, the limit slot 58 may be an arcuate groove. For example, the arcuate groove may be arcuate, or the like. The axis of the circular arc shape may be co-linear with the center of rotation of the clamping holder 52. With the arcuate groove, the elastic deformation of the limit block 59 may keep constant during the relative movement of the limit block 59 with the limit slot 58, which is favorable to prolonging the service life of the limit block 59.

In some embodiments, the limit slot 58 may be a through slot through the support seat 51. At least a portion of the limit block 59 may extend out of the support seat 51 through the limit slot 58 to facilitate observation of the position of the limit block 59 relative to the limit slot 58 from an outside perspective and allow the limit block 59 to be operated from the outside of the support seat 51.

In some embodiments, the limit block 59 may be rotationally connected to the clamping holder 52. The limit block 59 may be rollingly connected to the limit slot 58.

By providing the guide wire delivery device, the guide wire may be guided, transported, and secured, and it is convenient for the guide wire to be loaded into the protective trocar. Using the first groove feature and the second groove feature, the limit slot and the limit block may form three different kinds of snap relationships, thereby enabling the guide wire delivery device to correspondingly form three different working states. Under different working states, the relative positions of the guide wire delivery gears and the guide wire are precisely controlled.

In some embodiments, the guide wire delivery device further includes a guide wire drive assembly.

The guide wire drive assembly may output power. For example, at least one of torque, turning force, or the like, may be output by the guide wire drive assembly. In some embodiments, the guide wire drive assembly may be drivingly connected to the guide wire delivery gear 57. The guide wire drive assembly may output a torque to drive the guide wire delivery gear 57. In some embodiments, the guide wire drive assembly may be provided on an outer side of a fixed structure 5. In some embodiments, the guide wire drive assembly may be manually controlled healthcare personnel. In this way, the delivery speed of the guide wire 17 is manually controlled, which facilitates the healthcare personnel to adjust the delivery speed or position of the guide wire 17 based on a requirement.

In some embodiments, the guide wire drive assembly may include at least one rotating shaft, the rotating shaft may be drivingly connected to the guide wire delivery gear 57 via a transmission chain, and the healthcare personnel may drive the guide wire delivery gear 57 to rotate by turning the rotating shaft. In some embodiments, the drive chain may include at least one of a gear drive chain, a belt drive chain, a chain drive chain, or the like.

By setting the guide wire drive assembly, the guide wire may be automatically delivered, which may effectively control the delivery speed of the guide wire, and may reduce the workload of the healthcare personnel and improve work efficiency.

In some embodiments, healthcare personnel may press the two adjusting plates 53 at the same time when performing a procedure, and the pressing of the adjusting plates 53 may drive the two clamping holders 52 to rotate outwardly so that the two clamping holders 52 are in an open state (as shown in FIG. 14). The healthcare personnel may slide one end of the guide wire 17 into the groove 511 along the inclined surface 523 of one of the clamping holders 52, and then precisely insert it into the protective trocar 8 through a gap between the two clamping holders 52. After the guide wire 17 passes through the protective trocar 8 with a certain length from the other end, the healthcare personnel may release the adjusting plates 53; at this time, the clamping holders 52 are rotated backwards under the action of the torsion springs 55 to be in the closed state (as shown in FIG. 12), so that the opposite-set fixing projections 56 are close to each other, thereby clamping the guide wire 17, so that the guide wire 17 may guide the movement of the trocar cutting knife 3 in the subsequent surgical procedure, which may facilitate fixation of the guide wire 17 to reduce the difficulty of the subsequent surgical procedure.

After fixation of the guide wire 17 is complete, the healthcare personnel may cut the skin at both ends of the vein to be harvested and cut off the vein, retaining the end vein ligature, and then extend the guide wire 17 into one of skin incisions and pass the guide wire 17 through the inside of the vein, and then lead the guide wire 17 through the other skin incision to lead out. The healthcare professional may drive the trocar cutting knife 3 to move along a direction away from the grip 1 using the drive mechanism, so that the trocar cutting knife 3 may be inserted into the tissue and cut the tissue around the vein to separate the tissue from the vein. The guide wire 17 may guide the trocar cutting knife 3. While cutting the tissue, the blood vessel separated from the tissue may enter into the protective trocar 8, and the blood vessel is always located inside the protective trocar 8, so as to protect the blood vessel by using the protective trocar 8, preventing the trocar cutting knife 3 from cutting the blood vessel. The trocar cutting knife 3 may be isolated from the outside world by the bacteriostatic cylinder 2 to avoid the trocar cutting knife 3 being in contact with the outside environment. The trocar cutting knife 3 may be sterilized by the ultraviolet lamp 4 disposed inside the bacteriostatic cylinder 2, which may play a highly effective role in bacteriostasis. The blood on the trocar cutting knife 3 may be cleaned by the cleaning mechanism 6 in the stretching and retracting process of the trocar cutting knife 3, which may avoid the growth of bacteria.

When the motor 13 is turned on, the output end of the motor 13 may drive the second gear 12 to rotate, the second gear 12 rotates to drive the first gear 11 to rotate, and the first gear 11 rotates to drive the threaded pipe 9 to rotate. Because the threaded pipe 9 is threadedly connected to the nut 10, and the nut 10 remains fixed, the threaded pipe 9 may move relative to the grip 1 when rotating, thereby driving the trocar cutting knife 3 to rotate while moving relative to the grip 1, so that the trocar cutting knife 3 may better cut the tissue.

When the healthcare personnel needs to replace the cleaning cotton 62, it is only need to unscrew the fixing cap 61 and then take out the cleaning cotton 62 for replacement, the size of the chamber formed between the fixing cap 61 and the bacteriostatic cylinder 2 may be adjusted by rotating the fixing cap 61, thereby adjusting the cleaning cotton 62 on the pressure of the trocar cutting knife 3, so as to adjust the cleaning strength. When the cleaning cotton 62 absorbs too much blood and affects the cleaning effect, a portion of the blood on the cleaning cotton 62 may be squeezed out by tightening the fixing cap 61. During operation, the fixing cap 61 may be tightened so that the fixing cap 61 compresses the cleaning cotton 62. At the same time, the fixing cap 61 moves to move the sealing ring 64 out of the through hole, so that the blood squeezed out of the cleaning cotton 62 may flow out through the through hole, and the blood can be squeezed out more conveniently for cleaning.

The basic concepts have been described above, and it is apparent to those skilled in the art that the foregoing detailed disclosure serves only as an example and does not constitute a limitation of the present disclosure. While not expressly stated herein, a person skilled in the art may make various modifications, improvements, and amendments to the present disclosure. Those types of modifications, improvements, and amendments are suggested in the present disclosure, so those types of modifications, improvements, and amendments remain within the spirit and scope of the exemplary embodiments of the present disclosure.

Also, the present disclosure uses specific words to describe embodiments of the present disclosure. Such as "an embodiment", "one embodiment", and/or "some embodiments" means a feature, structure, or characteristic associated with at least one embodiment of the present disclosure. Accordingly, it should be emphasized and noted that "an embodiment" or "one embodiment" or "an alternative embodiment" in different places in the present disclosure do not necessarily refer to the same embodiment. In addition, certain features, structures, or characteristics of one or more embodiments of the present disclosure may be suitably combined.

Finally, it should be understood that the embodiments described herein are only used to illustrate the principles of the embodiments of the present disclosure. Other deformations may also fall within the scope of the present disclosure. As such, alternative configurations of embodiments of the present disclosure may be viewed as consistent with the teachings of the present disclosure as an example, not as a limitation. Correspondingly, the embodiments of the present disclosure are not limited to the embodiments expressly presented and described herein.

What is claimed is:

1. An efficient bacteriostatic minimally invasive collection device for great saphenous vein, comprising a grip, a trocar cutting knife, and a protective trocar; wherein
the protective trocar is disposed inside the trocar cutting knife, the trocar cutting knife is rotationally connected to the protective trocar;
the protective trocar passes through the grip;
the grip is provided with a drive mechanism for driving the trocar cutting knife to move relative to the grip;
a bacteriostatic cylinder is fixedly mounted at one end of the grip, and the trocar cutting knife passes through the bacteriostatic cylinder;
an ultraviolet lamp is fixedly mounted inside the bacteriostatic cylinder, and an end of the bacteriostatic cylinder is provided with a cleaning mechanism for cleaning the trocar cutting knife;
the cleaning mechanism includes a fixing cap and a cleaning cotton;
the fixing cap is threadedly mounted on the end of the bacteriostatic cylinder, the cleaning cotton is disposed in a shape of a ring, the trocar cutting knife passes through the cleaning cotton, and an inner annular wall of the cleaning cotton is in contact with an outer wall of the trocar cutting knife; and a plurality of fixing columns are fixedly mounted on an end wall of the bacteriostatic cylinder, a through-hole is opened in a bottom wall of the fixing cap, a blocking ring is disposed in the through-hole, a bottom end of the fixing columns is fixedly connected to the blocking ring, and the trocar cutting knife passes through the blocking ring.

2. The efficient bacteriostatic minimally invasive collection device for great saphenous vein according to claim 1, wherein the drive mechanism includes a threaded pipe and a nut;

the threaded pipe is sleeved on the outer wall of the trocar cutting knife and disposed inside the grip;

the nut is fixedly mounted inside the grip, the threaded pipe passes through the nut, and the threaded pipe is threadedly connected to the nut; and one end of the threaded pipe away from the nut is sleeved with a first gear, and a drive assembly for driving the first gear to rotate is disposed inside the grip.

3. The efficient bacteriostatic minimally invasive collection device for great saphenous vein according to claim 2, wherein the drive assembly includes a second gear and a motor;

the second gear is rotationally mounted inside the grip and meshes with the first gear; and the motor is fixedly mounted inside the grip, and an output end of the motor is drivingly connected to the second gear.

4. The efficient bacteriostatic minimally invasive collection device for great saphenous vein according to claim 3, wherein one or more limiting columns are fixedly mounted inside the grip; and at least one of the limiting columns is slidably provided with a slide ring, and the slide ring is fixedly connected to an outer wall of the protective trocar through a connecting bar.

5. The efficient bacteriostatic minimally invasive collection device for great saphenous vein according to claim 1, wherein a fixing mechanism for fixing a guide wire is disposed at a top region of the grip;

the fixing mechanism includes a support seat; and the support seat is coaxially disposed with the trocar cutting knife and provided with a groove, the groove is connected to an inner cavity of the grip, two clamping holders are symmetrically disposed in the groove and rotationally connected to the support seat through two connecting columns, the two connecting columns are sleeved with a torsion spring, respectively, and an adjusting plate is fixedly mounted on a side wall of at least one of the two clamping holders.

6. The efficient bacteriostatic minimally invasive collection device for great saphenous vein according to claim 5, wherein each of the two clamping holders includes a clamping portion and a rotating portion;

the one or more connecting columns are fixedly mounted on the rotating portion, and the clamping portion is disposed in a triangle shape; and the clamping portion is provided with an inclined surface, and the inclined surface is provided with a plurality of fixing projections.

* * * * *